United States Patent
Maeji et al.

(10) Patent No.: US 11,726,095 B2
(45) Date of Patent: *Aug. 15, 2023

(54) CONJUGATING MOLECULES TO PARTICLES

(71) Applicant: Anteo Technologies Pty LTD, Queensland (AU)

(72) Inventors: Nobuyoshi Joe Maeji, Queensland (AU); Chang-Yi Huang, Queensland (AU)

(73) Assignee: ANTEO TECHNOLOGIES PTY LTD, Queensland (AU)

( * ) Notice: Subject to any disclaimer, the term of this patent is extended or adjusted under 35 U.S.C. 154(b) by 610 days.

This patent is subject to a terminal disclaimer.

(21) Appl. No.: 14/907,701

(22) PCT Filed: Aug. 13, 2014

(86) PCT No.: PCT/AU2014/050181
§ 371 (c)(1),
(2) Date: Jan. 26, 2016

(87) PCT Pub. No.: WO2015/021509
PCT Pub. Date: Feb. 19, 2015

(65) Prior Publication Data
US 2016/0178636 A1    Jun. 23, 2016

(30) Foreign Application Priority Data

Aug. 13, 2013 (AU) ................................ 2013903093

(51) Int. Cl.
| | | |
|---|---|---|
| *G01N 33/58* | (2006.01) | |
| *G01N 33/543* | (2006.01) | |
| *G01N 33/553* | (2006.01) | |
| *C07K 17/14* | (2006.01) | |
| *C07K 1/13* | (2006.01) | |

(52) U.S. Cl.
CPC ............. *G01N 33/587* (2013.01); *C07K 1/13* (2013.01); *C07K 17/14* (2013.01); *G01N 33/54326* (2013.01); *G01N 33/553* (2013.01)

(58) Field of Classification Search
CPC .......... G01N 33/587; G01N 33/54326; G01N 33/553; C07K 17/14; C07K 1/13
See application file for complete search history.

(56) References Cited

U.S. PATENT DOCUMENTS

| 5,981,286 A | 11/1999 | Herrmann et al. |
|---|---|---|
| 9,234,891 B2* | 1/2016 | Muir ................. G01N 33/54353 |
| 10,768,176 B2* | 9/2020 | Huang ................. G01N 33/553 |
| 10,786,606 B2* | 9/2020 | Maeji ................. A61L 33/0011 |
| 2008/0241963 A1 | 10/2008 | Lin et al. |
| 2011/0135571 A1* | 6/2011 | Lin ....................... A61K 31/555 |
| | | 424/1.65 |
| 2017/0115285 A1* | 4/2017 | Huang ................. G01N 33/553 |

FOREIGN PATENT DOCUMENTS

| JP | 05-502944 | 2/2004 |
|---|---|---|
| WO | WO2004/036189 | 4/2004 |
| WO | WO 2005/065081 A2 | 7/2005 |
| WO | WO 2006/002472 A1 | 1/2006 |
| WO | WO 2011/044545 A2 | 4/2011 |
| WO | WO 2011/046842 A1 | 4/2011 |
| WO | WO 2011/140590 A1 | 11/2011 |
| WO | WO 2012/012748 A2 | 1/2012 |

OTHER PUBLICATIONS

Abernethy et al. ("Metal Polymers, a Glue to Immobolise Proteins Onto Synthetic Surfaces", Poster dated Apr. 30, 2012) (Year: 2012).*
Muir et al. ("High-throughput optimization of surfaces for antibody immobilization using metal complexes", Anal. Biochem., vol. 363, pp. 97-107, published 2007) (Year: 2007).*
Hauserman et al. ("Chromium Complexes," Advances in Chemistry, vol. 23, chapter 32, pp. 338-356, published Jan. 1, 1959) (Year: 1959).*
Xi Li et al., "Enhancement of cell recognition in vitro by dual ligand-cancer targeting gold nanoparticles," *Biomaterials* (2011) 32 (10): 2540-2545.
Anonymous: "Technical Manual MagneHis(TM) Protein Purification System, Instructions for use of products V*500, V8550, V8560 and V8565", Promega, Jul. 23, 2013 (cited in Supplementary European Search Report of Feb. 23, 2017).
Henrique E. Toma et al. "The coordination chemistry at gold nanoparticles" Journal of the Brazilian Chemical Society, vol. 21 (7), p. 1158-1176. This was cited in the European Opinion Apr. 9, 2018.

* cited by examiner

*Primary Examiner* — Shafiqul Haq
*Assistant Examiner* — Nam P Nguyen
(74) *Attorney, Agent, or Firm* — Charles C. Achkar; Ostrolenk Faber LLP

(57) ABSTRACT

This invention resides in using metal complex-activated particles to bind molecules, polymers and other particles to each other, so as to produce multifunctional conjugates having controlled ratios of two or more different molecules.

13 Claims, 18 Drawing Sheets

CONJUGATING MOLECULES TO PARTICLES

CROSS-REFERENCE TO RELATED APPLICATIONS

This application is a National Stage Application, filed under 35 U.S.C. § 371, of International Application No. PCT/AU2014/050181, filed on Aug. 13, 2014, which claims priority to, and the benefit of, Australian Patent Application No. 2013903093, filed on Aug. 13, 2013. The contents of each of these applications are incorporated herein in their entireties.

FIELD OF THE INVENTION

The present invention relates to reagents and methods for linking target molecules (such as antibodies, enzymes, streptavidin, Protein A, Protein G, a lipoprotein or a glycoprotein) with other molecules (such as other proteins, labels, dyes, synthetic polymers and/or nanoparticles).

More specifically, the invention relates to methods for designing and producing particle conjugates having controlled ratios of two or more molecules (such as biomolecules, labels, dyes, synthetic polymers and/or nanoparticles).

BACKGROUND OF THE INVENTION

There is a need for simple processes to link biomolecules such as peptides, proteins, polynucleotides and carbohydrates with each other, or with small molecule and biological (for example, protein and polynucleotide) drugs, dyes, labels, synthetic polymers and nanoparticles, in many applications in life sciences research, such as drug discovery and diagnostics. There are many approaches in the prior art (such as those described in Hermanson, et al., *Bioconjugate Techniques*: Academic Press, 1996).

In brief, two key requirements in forming multi-functional conjugates with biomolecules are minimisation of any damage to the function of the biomolecules, and control over the ratio of the two or more molecules forming the conjugate. Depending on the application and the size of the molecules being linked to each other, there may be the need to have only one molecule of each type conjugated to each other. The alternative is to have multiple molecules of one type conjugated to a larger biomolecule. For example, if molecules A and B need to be linked to each other to form A-B with no functional damage, obtaining 3 (A-B)s is not so trivial at the molecular level. It is very possible that one A can link with 1, 2 or more Bs and similarly one B may link with 1, 2 or more As. It is possible that A and B can link with themselves, and as well, as a consequence of multiple linking, there will also be As and Bs that will not be able to form a link with another molecule at all. There is a population of different entities produced, depending on the molecules being conjugated and the methodology being used, and under most circumstances, achieving uniformity and consistency between different batches is a challenging process.

Many different linker chemistries have been used in an attempt to minimise difficulties in consistency and reproducibility in forming conjugates with biomolecules. One completely different approach to forming conjugates would be to link different molecules to a common carrier, such as some nano- or microsize particle as opposed to directly linking such molecules. For example, carboxylic acids can be generated on particle surfaces for reaction with biomolecules containing amino groups, a maleimide or a bromoacetamido group can be generated on particles for reaction with thiols, and almost any linking strategy can be applied to particle surfaces to form conjugates of two or more different molecules. However, as the particle gets smaller and smaller, the same problems of uniformity and reproducibility appear. Generating different functionalities on particle surfaces to give orthogonal coupling can potentially solve such difficulties but in the end, formation of different functional groups needs to start from some common starting group on the particle and the same problems of uniformity and reproducibility appear again.

An example of the type of linking strategies discussed above is given in Lim, I-I. S. et al. (2008) *Nanotechnology*, vol. 19, p. 1-11, which describes the synthesis and characterisation of protein-capped gold and magnetic oxide/gold core/shell nanoparticles. The systems described in this article all use dithiobis (succinimidyl propionate) (DSP) to bind the proteins to the nanoparticles. Ideally, for the reasons given above, a new method of forming conjugates should not require the use of these types of linking agents.

Reference to any prior art in the specification is not, and should not be taken as, an acknowledgment or any form of suggestion that this prior art forms part of the common general knowledge in any jurisdiction or that this prior art could reasonably be expected to be understood and regarded as relevant by a person skilled in the art.

SUMMARY OF THE INVENTION

The present inventors have found that nano- and microparticles of the invention are able to bind molecules, polymers and other particles to achieve a predetermined and desired multifunctional entity comprising different molecules in specific ratios to each other.

Accordingly, the present invention relates to a particle including:
  a surface;
  transition metal ions at least partially coating the surface; and
  a first target molecule and a second target molecule, wherein the first and second target molecules are different to each other,
wherein the particle is formed from one or more substrate molecules or multiple atoms, and wherein the transition metal ions form co-ordination bonds with the substrate molecules or atoms at the particle surface, and at least one of the first target molecules and at least one of the second target molecules, thereby linking the first and second target molecules to the particle.

In one embodiment, the particle is a nanoparticle.

The present invention also relates to a composition including:
  a particle formed from one or more substrate molecules or atoms;
  a ligand having a group for forming a co-ordination bond with a transition metal ion;
  a transition metal ion for forming a co-ordination bond with the one or more substrate molecules or atoms.

In one embodiment, the particle included in the composition does not have a linker attached to a substrate molecule or atom for binding with the transition metal ion. The composition may further include a first target molecule and a second target molecule, wherein the first and second target molecules are different to each other.

In one embodiment, the particle is a nanoparticle.

The present invention also relates to a particle formed from a plurality of transition metal ions, the particle including:
- a surface; and
- a first capture molecule and a second capture molecule, wherein the first and second capture molecules are different to each other, wherein the transition metal ions of the particle form, at the particle surface, co-ordination bonds with the first and second capture molecule, thereby linking the first and second capture molecules with the particle.

In one embodiment, the first capture molecule is selected from a protein, polynucleotide, carbohydrate, and drug.

In one embodiment, the second capture molecule is selected from a protein, carbohydrate, lipid, polynucleotide, drug, labelling agent, synthetic polymer and nanoparticle. The protein may be an antibody or fragment thereof.

In one embodiment, the particle is a nanoparticle.

The present invention also relates to a process for linking a first target molecule to a second target molecule, the process including:
- providing transition metal ions;
- providing a particle, wherein the particle has a surface and is formed from one or more substrate molecules or atoms that embody the particle;
- providing the first target molecule and the second target molecule in a pre-determined ratio;
- contacting the transition metal ions and the particle with the first and second target molecules such that the transition metal ions form co-ordination bonds with the substrate molecules or atoms at the particle surface, and at least one of the first target molecules and at least one of the second target molecules, thereby linking the first and second target molecules to each other by means of the particle.

In one embodiment, the first capture molecule is selected from a protein, polynucleotide, carbohydrate, and drug.

In one embodiment, the second capture molecule is selected from a protein, carbohydrate, lipid, polynucleotide, drug, labelling agent, synthetic polymer and nanoparticle. The protein may be an antibody (or a fragment thereof).

In one embodiment, the particle is a nanoparticle.

DETAILED DESCRIPTION OF THE INVENTION

Figure 1:
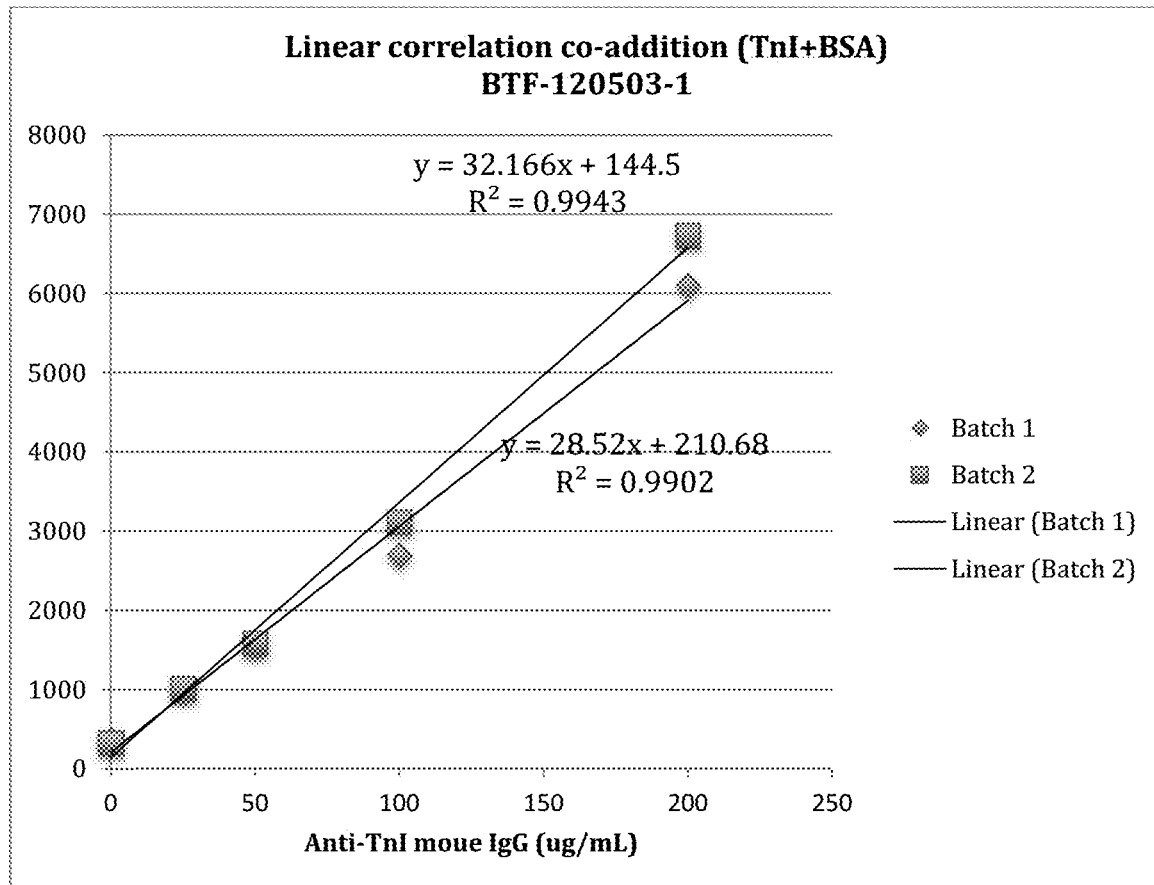
FIG. 1. The amount of antibody added to a suspension of metal complex-activated 500 nm particles was proportional to the signal output (fluorescence unit, y-axis) from FACS Canto II.

In general terms the present invention resides in the surprising finding that using metal complex-activated nano- and microparticles (that are capable of high reactivity) can be used to bind molecules, polymers and other particles so as to produce multifunctional entities comprising different molecules. Importantly, the ratio of these molecules on each particle can be controlled to give a consistent distribution of particles, across the particle population, having particular ratios of the different molecules attached thereto.

One method of linking biomolecules to various surfaces is to use metal complexes such as those used for Immobilised Metal Affinity Chromatography (IMAC), which is a well-known technique, or methods as described in PCT/AU2005/00966 (published as WO 2006/002472). In particular, metal complexes as described in the PCT application allow strong but gentle binding interactions that minimise damage to biomolecules (such as proteins) on all sorts of different surfaces.

In this respect, the metal complex-activated particle may be regarded as being a form of cross-linking agent that facilitates binding of different molecules, polymers or particles, via a micro- or nanoparticle, to each other. In essence, the metal complex-activated nano- or microparticle acts as a mediator which controls the overall number, density and proportion of the different molecules forming the multifunctional entity. Assuming the entity is of the form, nA-X-mB, where X is the particle, and A and B are, for example, different biomolecules, polymers or nanoparticles, the intention is to achieve a stable (i.e. non-reversible) binding interaction between the components of the entity, where "n" and "m" can be adjusted with respect to each other and X. The ratios of the different molecules, i.e., A and B (and C, etc.) ultimately bound to the particle are adjustable according to the ratio in which the molecules are mixed with particle X because there is a strong correlation between what is added to solution to what actually is bound to the particle.

It will be appreciated from the foregoing that the metal complex-activated particles useful in the practice of the present invention are ones that are capable of undergoing rapid binding to biomolecules, thereby achieving a desirable, reproducible ratio of different molecules, polymers, and other nanoparticles, under the conditions (such as pH, temperature, ionic strength, etc.) at which these species are exposed to each other, and under the conditions associated with the practical application (e.g. an assay, a diagnostic test, drug delivery) in which the methodology of the invention is employed. In this respect the metal complex-activated particles, as a consequence of the coating process, are more likely to be positively charged and the molecules binding to the metal complex-activated particles can be rendered more electronegative by altering the prevailing conditions (for example, buffer, pH, etc). This means, for example, that the binding kinetics of the different molecules binding to the metal complex-activated particles can be further adjusted to obtain the desired ratio of molecules within the entity.

As used herein, the terms "target molecule" and "capture molecule" refer to any molecule that it is desired to be immobilised on the particle. In an embodiment of the present invention, the target molecule or capture molecule is selected from biological molecules, drugs, small molecules and labelling agents. Examples of biological molecules include proteins, polynucleotides, carbohydrates and lipids. The invention has particular applicability in relation to antibodies as the target or capture molecule. However, the terms "target molecule" and "capture molecule" may embrace any molecule that is desired to be linked to a particle surface. For example, the target or capture molecule may be a protein, such as an antibody (or a fragment thereof), an enzyme (such as horseradish peroxidase), streptavidin, Protein A, Protein G, a lipoprotein or a glycoprotein. Examples of polynucleotides include DNA and RNA. Suitable carbohydrates include polysaccharides (whether substituted or unsubstituted). The target or capture molecule may also be selected from a polynucleotide, a lipid, a carbohydrate, a drug, a labelling agent, a synthetic polymer and a nanoparticle.

The target molecule or capture molecule can be any molecule with electron donating potential to form stable co-ordination bonds to the metal ion of the metal complex. In one embodiment, the target or capture molecule is bound directly to the metal ion (i.e. it is not modified prior to use in the present invention). In another embodiment, the target or capture molecule or the ion includes a linker that binds the target molecule to the metal ion via the linker. Examples of linkers include those discussed in Lim, I-I. S. et al (mentioned above) and WO 2012/012748.

In one embodiment, the target or capture molecule is also a particle (e.g. a nanoparticle or a microparticle).

As discussed throughout the specification, the present invention seeks to provide a particle species having more than one type of molecule (for example, an antibody and a drug, a carbohydrate and a labelling agent, or a polynucleotide and a nanoparticle) bound to the particle. In these examples, an antibody is different to a drug, a carbohydrate is different to a labelling agent, etc, and it is in this context that the target/capture molecules are said to be different. However, it will also be understood that both the first and the second target/capture molecules could be, for example, antibodies, but different antibodies. Therefore, in the context of the present invention, the use of "different" target/capture molecules includes the case where the molecules are of different classes and where the molecules are of the same class but are different (e.g. both are antibodies but bind different antigens).

As used herein, the term "particle" refers to a small object that behaves as a whole unit with respect to its transport and properties i.e. a discrete unit of matter, where the atoms or molecules from which it is formed essentially embody the particle. By "nanoparticle" it is intended to mean particles having a diameter below about 1000 nm (for example, about 500 nm) and more specifically below about 300 nm. Preferably, the diameter of the nanoparticle is less than about 250 nm (for example, less than about 220 nm). A diameter range of between about 5 and about 200 nm is suitable. In one embodiment, the term "nanoparticle" refers to particles having diameters in the nano size range, which do not cross over into the micron size range.

Generally, the particle used in accordance with the present invention will be a nanoparticle. However, where the target/capture molecules to be linked are larger (and steric hindrance therefore makes the use of nanoparticles impractical) a larger particle (such as a microparticle) may need to be used. Where the particle is a microparticle, typical sizes suitable for use in the present invention include microparticles of less than about 10 micrometers (for example, 5 micrometers or less, or 3 micrometers or less).

In the formulation of the multifunctional entity of the present invention (for example, nA-X-mB where A, B and X may perform different functions), there is no restriction on the relative sizes of the individual components. In one embodiment of the invention, the metal complex-activated nanoparticles may be very small and are bound to a mixture of smaller proteins (A) and larger nanoparticles (B). In that case, the entity may consist of proteins on nanoparticles on larger nanoparticles. In another embodiment, the metal complex-activated nanoparticle is larger in size than the binding molecules, giving a particular ratio of molecules on this nanoparticle to form the multifunctional entity.

Any nanoparticle or microparticle known in the art can be used in the present invention. Examples of suitable nanoparticles and microparticles include those composed of metals (such as gold, silver, platinum, iridium, titanium and aluminium), synthetic polymers (e.g. polystyrene, cyclic olefin copolymers, polycarbonates, polyvinyl ethers, polyacrylamides, polymethacrylates, polyvinylidene fluorides and polyvinylalcohols), biological materials (e.g. bio-polymers including substituted polysaccharides such as nitrocellulose, cellulose acetate, etc), metal or metalloid composites (e.g. comprising the metals mentioned above, as well as steel, ceramics, silica and those used to produce materials such as QDots), glass, ceramics, metal oxides (such as iron oxide, titanium oxide, and silver oxide), silicon and carbon.

Magnetic particles, which can be composed of one or more of the species mentioned above, are also intended to be within the scope of the term "particle". Therefore, the particles may be formed from a heterogeneous mixture of substrate molecules or a heterogeneous mixture of atoms, or may be formed from one type of atom. In one embodiment, the particle defines a substantially spherical form.

In addition to the above, biological particles can also be utilised as "particles" in accordance with the present invention. Examples of these include viral particles (which normally have a size of 20 nm to 300 nm), virus-like particles (e.g. particles that are composed of only the shell of a viral particle), HDL and LDL nanoparticles (which normally have a size of 5-30 nm), self-assembled nanoparticles, proteins, bacterial particles, and cells (including single cell bacteria and red blood cells). Any such particles that can be coated with a metal complex and then subsequently bound to labels or other nanoparticles to carry functional moieties can be used in accordance with the present invention. The modified particles can act as a carrier to carry genetic information or a drug, and bind to a target cell or site to release the genetic material or drug inside the cell. The metal complex-activated particles can also bind to iron oxide nanoparticles to make the particles magnetic, so as to facilitate subsequent separation and purification during surface modification.

The method of the present invention involves exposing a metal complex-activated particle to at least two or more molecules, polymers, or other particles (e.g. nanoparticles), in a predetermined ratio, to obtain an entity having the desired ratio of molecules on the particle. Selection of a suitable metal complex(es) to form the metal complex-activated particle will depend upon a variety of factors. The mechanism by which the metal complex-activated particle binds to the different molecules, or rather to a region of the different molecules, is believed to involve both electrostatic attraction and subsequent displacement by the molecule of one or more ligands associated with the metal complex. For this to occur the molecules must be able to form preferential associations with the metal atom of the metal complex when compared to one or more existing coordinate ligands that are already in association with the metal complex prior to interaction with the molecule. It is possible in accordance with an embodiment of the invention to manipulate the binding characteristics of the metal complex nanoparticle with respect to the molecules in order to achieve the desired binding interaction with the molecules. This can be done by, for example, changing the environment around the transition metal (e.g. by including, or changing, ligands co-ordinated to the transition metal ion).

As used herein, the term "transition metal ion" refers to an element whose atom has an incomplete d sub-shell, or which can give rise to cations with an incomplete d sub-shell. Metal ions that may be used are selected from the group consisting of aluminium, rhodium, scandium, titanium, vanadium, chromium, ruthenium, platinum, manganese, iron, cobalt, nickel, copper, molybdenum, zirconium and zinc ions. Chromium, ruthenium, iron, cobalt, aluminium, zirconium and rhodium are preferred. Particularly preferred is chromium and further, where the chromium has an oxidation state of III. Other oxidation states of chromium include I, II, IV, V and VI. Where the coating layer includes chromium, the coating layer may further include transition metal ions other than chromium. In addition, mixtures of different metal ions may be used (for example, the surface may be coated with two or more, three or more, or four or more different metal complexes that include different metal ions).

As noted above, the transition metal ion may partially or fully coat the particle (i.e. the particle will be "metal complex-activated"). Alternatively, the particle may be composed of the transition metal. A chromium oxide nanoparticle is an example of the latter embodiment. Accordingly, the present invention also relates to a particle formed from a plurality of transition metal ions, the particle including:
a surface; and
a first capture molecule and a second capture molecule, wherein the first and second capture molecules are different to each other,
wherein the transition metal ions of the particle form, at the particle surface, co-ordination bonds with the first and second capture molecules, thereby linking the first and second capture molecules with the particle.

In one embodiment, the first capture molecule is selected from a protein, polynucleotide, carbohydrate, and drug. That is, the first molecule is a molecule having selectivity and specificity for a particular ligand (for example, an antibody that binds an antigen, a nucleic acid strand that binds a complementary nucleic acid strand, or other specific binding reactions, such as biotin binding streptavidin).

A transition metal ion on the particle surface may be associated with one or more co-ordination ligands (in addition to the target/capture molecule discussed above). In principle, any species that includes an electron-donating group can act as a ligand. In addition, a "ligand" can include any species that can link transition metal ions together or displace one co-ordination ligand with another. A relevant ligand may also assist or facilitate the oligomerisation of metal oxide species on a particle surface. For example, a chromium metal oligomer of up to 10 to 12 chromium atoms could be linked with another metal-based oligomer by an appropriate co-ordination ligand. Accordingly, the surfaces of the particles of the present invention can include metal complexes and metal ions in the form of oligomers.

Typically, the surface of a particle will already contain groups that can act as ligands (such as oxides, in the case of metal-based particles, counter-ions such as citric acid that are often associated with metal nanoparticles such as gold, and hydroxyl, carboxylic acids and other functional groups commonly present in latex and other synthetic nanoparticles). However, it will be understood that other ligands may be added to the particle to form a particular type of metal complex on the particle surface. By selecting for particular ligands, the properties of the complex can be changed, which makes it possible to tune the binding interaction between the particle and the target molecule. Suitable ligands in this regard are any ligands capable of forming a co-ordination bond with the transition metal ion (such as compounds containing acid or amine groups). Examples of ligands that may be used include ethylenediamine, tetramethylethylenediamine, iminodiacetic acid, nitrilotriacetic acid, triphenylphosphine, oxalic acid, 1,10-phenanthroline, 8-hydroxyquinoline, salicylic acid, chloride, acetate, bromide, nitrate, perchlorate, alum, sulphate and pyridine. Ethylenediamine is preferred.

Where the transition metal ion is part of the particle itself, at least one of the capture molecules will be bound via co-ordination bonds directly to the nanoparticle surface. That is, a separate metal complex interface (such as a linker) is not required.

The present inventors have found that one advantageous characteristic of multiple metal complexes (i.e. numerous single metal ions or numerous oligomers made up of metal ions) is their reaction kinetics. Essentially, a film or coating of metal complexes forms a positively charged surface to give strong charge interactions with biomolecules, followed by co-ordination forces to form chelated metal complexes. Therefore, two binding forces work together to immobilise biomolecules on to the metal complexes on the particle surface. In addition, multi-valency (i.e. multiple interactions between electron donating groups on the molecule and multiplicity of metal ions on the surface) also adds greatly to the speed of binding. This all results in a very fast rate of reaction.

In contrast, most common linking methods (such as covalent binding and passive binding) do not use electrostatic attraction and simply depend on diffusion to place the complementary reacting groups in proximity to each other for a reaction between them to occur. In addition, covalent binding is dependent on the concentration of the groups available for reaction, and passive binding is often dependent on the concentration of the capture/target molecules (i.e. you may need significantly more of one target/capture molecule to achieve a ratio of 1:1 of one target molecule to another target molecule on a particle). Further, of those systems that rely on electrostatic attraction (such as coating negatively charged particles with positively charged polymers), stability of such systems is an issue because the reaction between the coating and the particle is reversible with variations in pH.

The present invention therefore relates to an alternative approach to conjugating molecules (such as biological molecules) to other molecules (such as other biological molecules, labels, dyes, synthetic polymers and/or nanoparticles), which is mediated by metal complexes on particles. Apart from very fast reaction kinetics, another advantage of metal complexes as used in the present invention is that multi-valency to chelate to electron donating groups present in biomolecules also means that the binding kinetics are similar across different biomolecules. Compared to conventional linking strategies, metal complexes on nanoparticles give far greater uniformity and reproducibility when linking two or more different biomolecules to the same nanoparticle. This is also the case for other combinations (e.g. biomolecules with synthetic polymers, smaller nanoparticles, etc). This is because the reaction kinetics of metal complexes on particles are such that what is added to the metal complex-activated particles will bind to the particles. In contrast, as mentioned above, conventional covalent chemistry depends on using an excess of biomolecules to drive the linking reaction.

By selecting different concentrations of two or more different molecules, it is possible, using the present invention, to achieve the desired ratio of incorporation of those two or more different molecules on a nanoparticle with greater certainty. The present invention allows the distribution of particles with particular ratios of target/capture molecules across the population of particles to be controlled. As the nanoparticle becomes smaller and smaller, this approach is believed to afford increased simplicity and reproducibility for linking two or more different molecules together. Accordingly, the present invention allows a molecule to be easily and efficiently conjugated with other molecules, labels, dyes, synthetic polymers and/or nanoparticles via metal complex nano- and microparticles, with a high degree of predictability and reproducibility. More specifically, the invention provides a way of designing and producing particles with very high reaction kinetics to bind different molecules to form multi-functional conjugates comprising different molecules on a particle.

The combination of nanoparticle, ligand and transition metal ion (and optionally target molecule), all as discussed above, can also exist in the form of a pre-prepared composition. For example, the composition may be an aqueous-based composition, which may contain other components, such as surfactants, buffers, etc. Alternatively, the composition may be a solid (for example, a dry powder), which is reconstituted by the addition of an appropriate liquid (e.g. water, a buffer solution, etc).

In another embodiment, there may be two or more different metal complex-activated particles binding to a molecule, polymer or another nanoparticle (by suitable exposure thereto), to form a multifunctional entity. In this case, the reactivity of the different metal complex-activated particles for the molecule is in proportion to the final ratio of the different metal complex-activated particles and molecules in the final multifunctional entity.

The present invention also relates to a process for linking a first target molecule to a second target molecule, the process including:
  providing transition metal ions;
  providing a particle, wherein the particle has a surface and is formed from one or more substrate molecules or multiple atoms that embody the particle;
  providing the first target molecule and the second target molecule in a pre-determined ratio;
  contacting the transition metal ions and the particle with the first and second target molecules such that the transition metal ions form co-ordination bonds with the substrate molecules or atoms at the particle surface, and at least one of the first target molecules and at least one of the second target molecules, thereby linking the first and second target molecules to by means of the particle.

The present invention will be exemplified with particular reference to the production and use of antibody and streptavidin (or enzyme) conjugates formed via metal complex nanoparticles. However, it will be appreciated that the underlying concepts of the invention are also applicable to microparticles, as well as in vitro diagnostics, in vivo imaging, drug delivery, drug discovery, bioprocessing, enzyme-mediated chemical reaction, and other applications where at least one (and possibly two or more) functions/activities need to be incorporated into the one entity. In addition, it will be appreciated that the transition metal may be a part of the nanoparticle itself (e.g. in the case where iron or gold nanoparticles are used). In this way, the formation of conjugates is simplified even further.

EXAMPLES

It will be understood that the invention disclosed and defined in this specification extends to all alternative combinations of two or more of the individual features mentioned or evident from the text or drawings. All of these different combinations constitute various alternative aspects of the invention.

Example 1: Binding Kinetics of Antibody and BSA on Metal Complex-Activate Magnetic Nanoparticles A. Metal Complex-Activated Nanoparticles.

As an example, magnetic nanoparticles of 500 nm dimensions (Ademtech MasterBeads, Cat No 0215) were coated with metal complexes as exemplified in PCT/AU2005/00966. In brief, chromium perchlorate hexahydrate (2.3 g) was dissolved into 25 mL of purified water and mixed thoroughly until all solid dissolved. Similarly, 545 µL of bis(3-aminopropyl)diethylamine solution was added to 25 mL of purified water. The solutions were combined and stirred for 2 days at room temperature (RT). The final solution was brought to pH 5.0 using sodium hydroxide and stirred overnight at room temperature.

Ademtech carboxyl-terminated magnetic particles (Lot. No. 10H005) were supplied from Ademtech, Pessac, France. To prepare the nanoparticles, they were allowed to reach room temperature and vortexed for 30 seconds. 124 μL of particle concentrate was dispensed into a microtube. The tube was placed on a magnetic rack for 1 minute and the supernatant was carefully removed and discarded from the particle pellet. The particle pellet was washed with 620 μl of deionised water, and after removing the supernatant, 620 μL of the above metal complex solution was added to reach a final concentration of 50 mM metal complex. This was left for 1 hour at RT with rotation.

B. Coupling a Mixture of Antibody and BA to Metal Complex-Activated Nanoparticles.

A mixture of antibody (Monoclonal mouse anti-cardiac troponin I (clone 19C7) from HyTest) and BSA (from AusGeneX, PBSA-Premium) (total of 20 μg per mg particles) were coupled to the metal complex-activated nanoparticle at 5 different ratios, i.e., 20 μg Ab and 0 μg BSA; 10 μg Ab and 10 μg BSA; 5 g Ab and 15 g BSA; 2.5 g Ab and 17.5 g BSA; 0 μg Ab and 20 μg BSA. In brief, the different antibody/BSA mixtures were prepared before use. The metal complex-activated Ademtech nanoparticles were taken from the rotor and the suspension was vortexed for 30 seconds. Tubes were placed on a magnetic rack for 1 minute and carefully removed. The supernatant was discarded and 620 μl 50 mM MES buffer pH 6.0 containing 0.0025% Triton X-100 (Wash Buffer) was added. Particles were sonicated for 1 minute and this MES wash step was repeated 2 times. Then 50 Id of washed particles was added into 5 separate microtubes, and tubes were placed on a magnetic rack for 1 minute. The supernatant was carefully removed and discarded. To each tube was added 50 μl of the each different antibody/BSA mixture. The particle solution was vortexed for 30 seconds. The tubes were incubated with rotation for 1 hour at RT. After vortexing the suspension for 30 seconds, tubes were placed on a magnetic rack for 1 min and carefully removed, and the supernatant was discarded from the bead pellet. To the bead pellet, 50 μL of Wash Buffer was added to the tube. The solution was vortexed, and washed 2 more times and blocked for immediate use or storage.

The antibody-loading assay on magnetic nanoparticles was performed according to the procedure below. In brief, the materials and methods are as described.

Assay Components:
  Antibody coupled particles;
  Detection Antibody: Goat anti Mouse-IgG (H+L)-FITC (1.5 mgs/mL, Jackson, USA);
  Assay Buffer: 50 mM TBS, pH 8.0 containing 0.05% Tween-20;
  Microplate: 96-well Greiner Polypropylene—U shape (Greiner bio-one, USA).

5 μl of each bead sample was diluted in 495 μL of Assay Buffer (50 mM TBS, pH 8.0 containing 0.05% Tween 20). After vortexing for at least 30 secs, 12 μL of suspension was removed and diluted again in 1188 μL of Assay Buffer. Goat anti-mouse IgG-FITC detection antibodies were diluted in Assay Buffer to working concentration of 2 μg/mL. After vortexing diluted bead suspension for at least 30 seconds, 100 μL of antibody coated particles was added to the wells followed by 100 μL of detection antibodies to the appropriate wells. The particles were incubated for 60 minutes at RT on the plate shaker in the dark. Beads were read on FACS Canto II (BD Biosciences, USA) and the results were shown in FIG. 1.

From FIG. 1, the signal was proportioned to the concentrations of anti-TnI antibody coupling to metal complex-activated 500 nm magnetic nanoparticles and showed a linear correlation. Co-coupling of BSA with the anti-TnI antibody, formed a common protein density where the protein ratios added determined the ratios coated and antibody distribution on particles. This demonstrated that the amount of capturing agent such as antibodies when coupling to the metal complex-activated surface can be controlled by simple protein titration in the coupling procedure without pH or time adjustments or chemical composition changes.

Example 2: Coating Antibody and Streptavidin on Metal Complex-Activated 200 nm Magnetic Particles The aim of this experiment was to demonstrate that 200 nm magnetic particles can be activated by a metal complex, and then be coupled with two macromolecules such as one type of antibody and streptavidin.

A. Preparation of Metal Complex-Activated 200 nm Magnetic Nanoparticles

Metal complex was prepared as exemplified in PCT/AU2005/00966. In this example, the version of 20 mM (final concentration) metal complex plus 0.1% Tween-20 was used. Commercially available 200 nm magnetic particles (M1-020/50 200 nm Merck magnetic carboxylated particles, Cat number: M1-020/50, Batch number: 7527/57) were activated by the metal complex at 10 mg/ml, by mixing the particles and metal complex at low speed vortexing for 10 seconds and bath-sonicating for 5 minutes, followed by incubation at RT with rotation for 2 hours. The microscopy observation showed that the metal complex-activated particles were mono-dispersed when compared to the un-activated particles (data now shown). This demonstrated the 200 nm magnetic particles can be activated by a metal complex and were fully dispersed in aqueous solution. The activated particles then were washed with Wash Buffer (25 mM MES pH 6, 0.05% ProClin 300 and 0.1% Tween-20) two times and then reconstituted in Coupling Buffer (25 mM MES pH 6 with 0.05% ProClin 300) before the protein-coupling step. The microscopy observation showed that washed particles were still mono-dispersed when compared to the un-activated particles (data not shown).

The 200 nm carboxylated magnetic particles were activated by the metal complex successfully and showed very good mono-dispersion.

B. Coupling of Streptavidin to Metal Complex-Activated Nanoparticles.

The coupling protein was prepared prior to use in coupling buffer (25 mM MES pH 6) as per the table below:

| | Streptavidin (μg per mg of particles) |
|---|---|
| Sample 2.1 | 120 |
| Sample 2.2 | 100 |
| Sample 2.3 | 80 |
| Sample 2.4 | 60 |

A tube with protein mixture was constantly vortexed on a low speed (No 3 setting on IKA Vortex GENIUS 3) while slowly adding 40 μL of washed particles to 60 μL of protein solutions to reach the concentrations listed in above table. The particle solution (10 mg/mL) was vortexed for 10 seconds and bath sonication for 1 minute. The particle solution was incubated with rotation (Rotator setting C1-speed 50 rpm) for 1 hour at room temperature. The particles were washed by storage buffer (50 mM TBS, 0.01% Tween 20, 0.05% ProClin 300, pH 8) 2 times and stored in 100 μL storage buffer at 4° C. Samples were assayed by binding to biotin-mouse IgG and detected by goat anti-mouse conjugated to horseradish peroxidase (GAM-HRP), read by multimode spectrophotometer (TECAN infinite M200PRO) with relative chemiluminescence unit as signal output as shown in FIG. 2.

Figure 2:
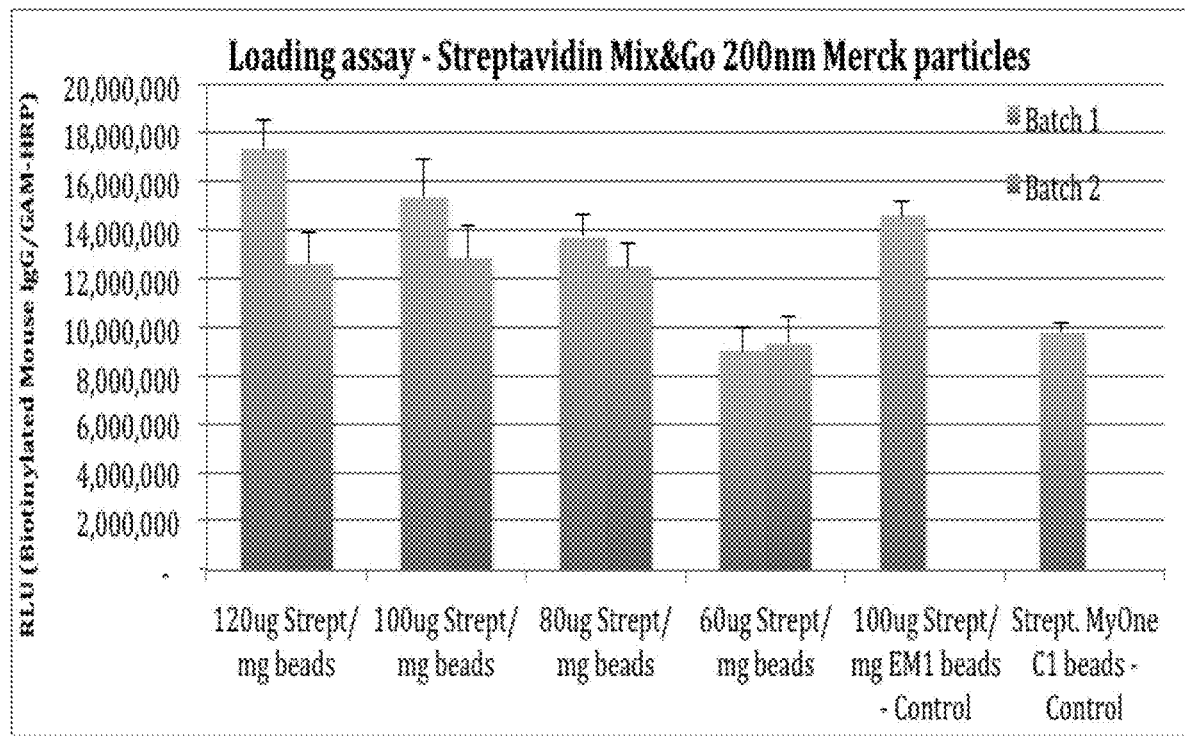
FIG. 2. Titration of streptavidin to metal complex-activated 200 nm particles—loading with biotinylated mouse IgG/GAM-HRP. The 1 μm magnetic particles (Merck and Dynal MyOne C1) coated with streptavidin are also shown.

The result from FIG. 2 showed that the signal output was related to the increase of streptavidin coupling concentrations. This result demonstrated that the amount of capturing agent such as streptavidin, when coupling to metal complex-activated surface, can be controlled by a simple protein titration step in the coupling procedure without additional pH or time adjustments or chemical changes.

C. Co-Coupling of Mouse IgG and Streptavidin

Nanoparticles activated by a metal complex were prepared according to section A, Example 2. The protein was prepared in a coupling buffer (25 mM MES pH 6), for final coupling concentration as per the table on the following page:

|  | Streptavidin (μg per mg of particles) | Mouse IgG (μg per mg of particles) |
| --- | --- | --- |
| Sample 2.5 | 70 | 30 |
| Sample 2.6 | 60 | 40 |
| Sample 2.7 | 50 | 50 |
| Sample 2.8 | 100 | 100 |
| Sample 2.9 | 50 | 50 |
| Sample 2.10 | 20 | 20 |
| Sample 2.11 | 10 | 10 |
| Sample 2.12 | 0 | 60 |

The tubes were constantly vortexed with protein mixture on a low speed (No 3 setting on IKA Vortex GENIUS 3) while slowly adding 40 μL of metal complex-activated particles to 60 μL of protein solutions to reach the concentrations listed in above table. The particle solution (10 mg/mL) was vortexed for 10 seconds and bath-sonicated for 1 minute. The particle solution was incubated with rotation (Rotator setting C1-speed 50 rpm) for 1 hour at room temperature. The particles were then washed twice with storage buffer (50 mM TBS, 0.01% Tween-20, 0.05% Proclin 300, pH 8) and stored in 100 μL storage buffer at 4° C. Samples (2.2, 2.5, 2.6, 2.7 and 2.12) were assayed by binding to biotin-mouse IgG and detected by goat anti-mouse conjugated to horseradish peroxidase (GAM-HRP), read by multimode spectrophotometer (TECAN infinite M200PRO) with relative chemiluminescence unit as signal output as shown in FIG. 3.

Figure 3:
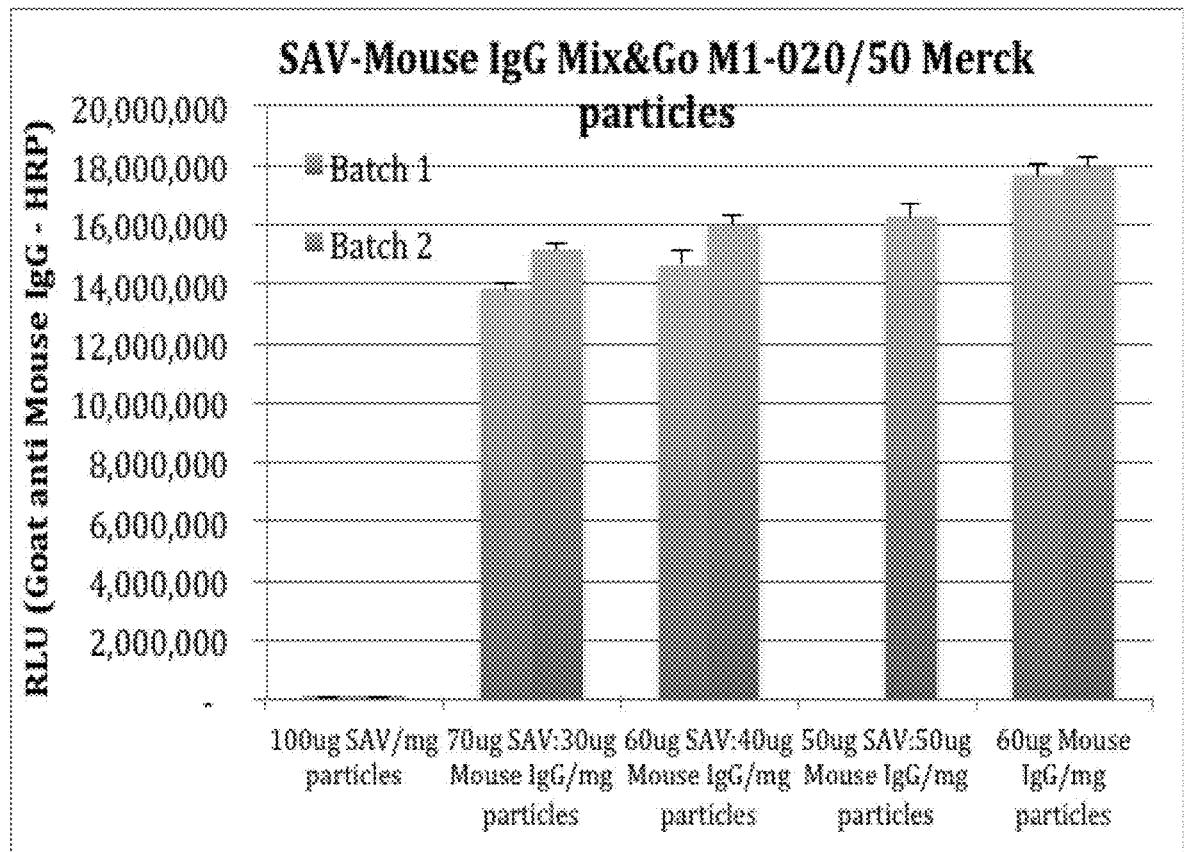
FIG. 3. Titration of streptavidin and mouse IgG to metal complex-activated 200 nm particles—loading with biotinylated mouse IgG/GAM-HRP.

The result from FIG. 3 showed that the signal output was related to the increase of mouse IgG coupling concentrations. The negative control (100 μg streptavidin per mg of particles) and positive control (60 μg mouse IgG per mg of particles) both showed the expected background and specific signal intensity. This result also demonstrated that the amount of macromolecule such as mouse IgG when co-coupling to metal complex-activated surface can be controlled by a simple protein titration step in the coupling procedure without additional pH adjustment or chemical changes.

Figure 4:
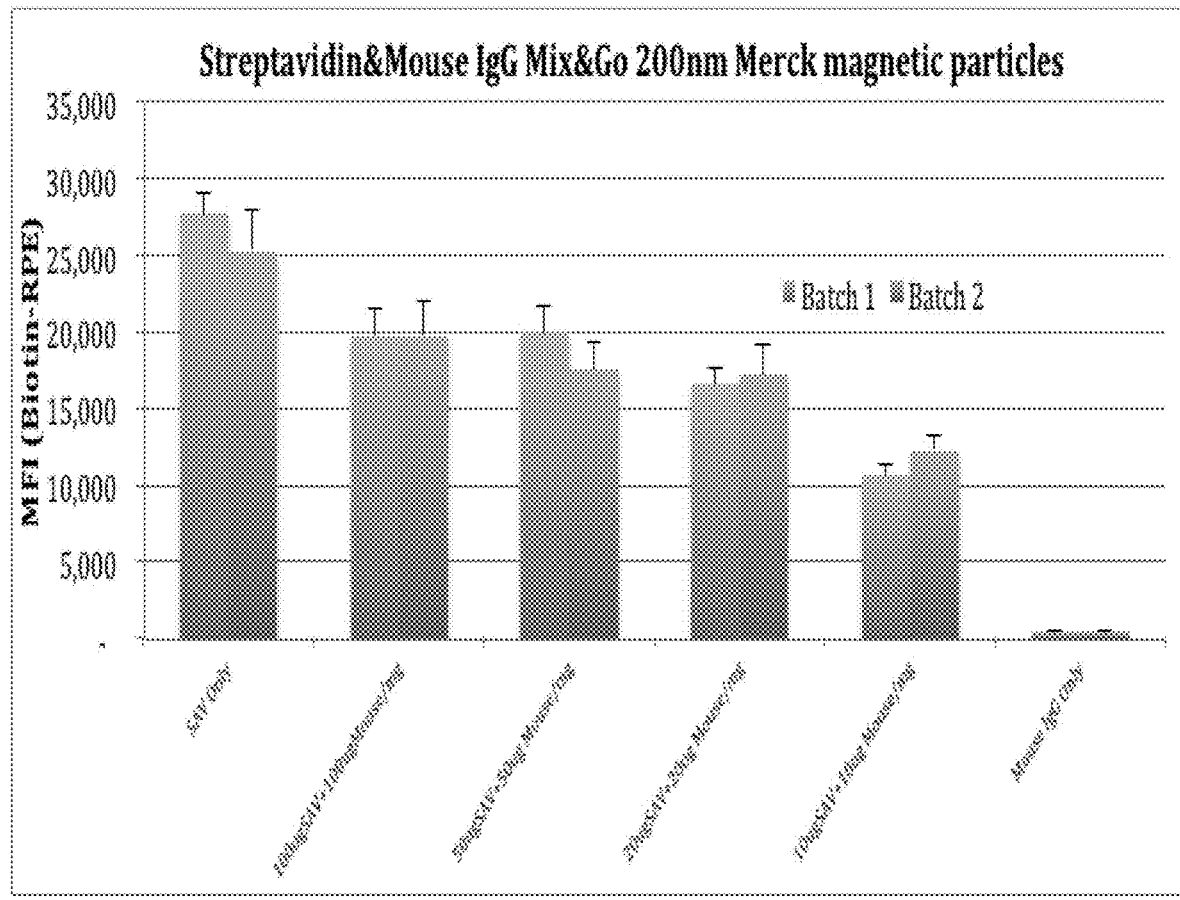
FIG. 4. Titration of streptavidin and mouse IgG to metal complex-activated 200 nm particles—loading with biotinylated RPE.

Samples (2.2, 2.8, 2.9, 2.10, 2.11 and 2.12) were assayed by binding to biotin-RPE, read by multimode spectrophotometer (TECAN infinite M200PRO) with relative fluorescence unit as signal output as shown in FIG. 4.

Figure 5:
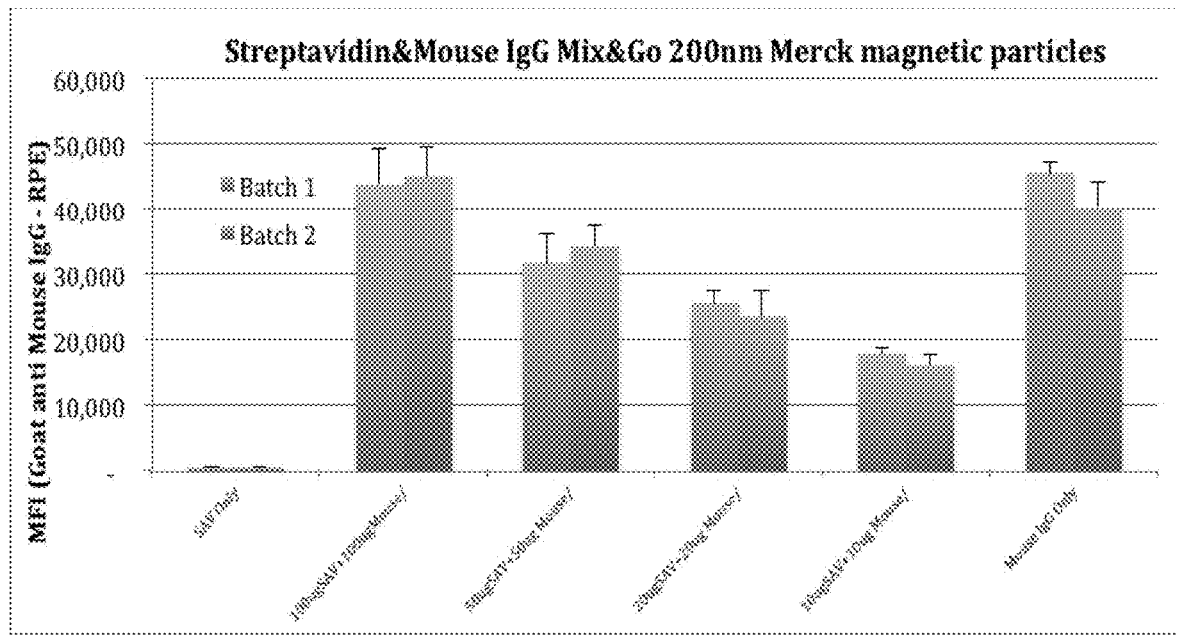
FIG. 5. Titration of streptavidin and mouse IgG to metal complex-activated 200 nm particles—loading with biotinylated mouse IgG and detected by goat anti-mouse RPE.

The result from FIGS. 4 and 5 showed that the signal output was related to the increase of mouse IgG or streptavidin coupling concentrations. In FIG. 4, the positive control (100 μg streptavidin/mg of particles) and the negative control (60 μg mouse IgG/mg of particles) were working well, and showed the expected signal intensity and background noise respectively. In FIG. 5, the negative control (100 μg streptavidin/mg of particles) and the positive control (60 μg mouse IgG/mg of particles) both showed the expected background and signal intensity respectively. This result also demonstrated that the amount of macromolecule (such as streptavidin and mouse IgG) used during the process of co-coupling to metal complex-activated surface can be controlled by a simple protein titration step in the coupling procedure without additional pH and time adjustments or chemical composition changes.

D. Performing Agglutination Assay on Streptavidin and Mouse IgG Co-Coupled with 200 nm Magnetic Particles D-1. Preparation Protein Coupled M270 Particles The co-coupling of biotinylated-goat anti-human IgG and BSA to metal complex-activated M270 particles were prepared by activating M270 carboxylated magnetic particles (Dynal) with 75 mM (final concentration) metal complex prepared according to section A, Example 2. M270 particles (25 mg/mL) were activated at room temperature for 60 minutes. The particles were washed three times by 25 mM MES pH 6. The antibody was coated at a concentration of 2.5 μg antibody per mg of activated particles. The coated particles were incubated at room temperature for 60 minutes. The antibody-coated particles were then blocked by 0.1% BSA in 25 mM MES buffer pH 6 at room temperature for 60 minutes and washed three times in TBS buffer pH 8 and stored at 4° C. in TBS buffer pH 8. The particles were assayed by binding to streptavidin-conjugated HRP and read by multimode spectrophotometer (TECAN infinite M200PRO) with relative chemiluminescence unit as signal output as shown in FIGS. 6 and 7.

Figure 6:
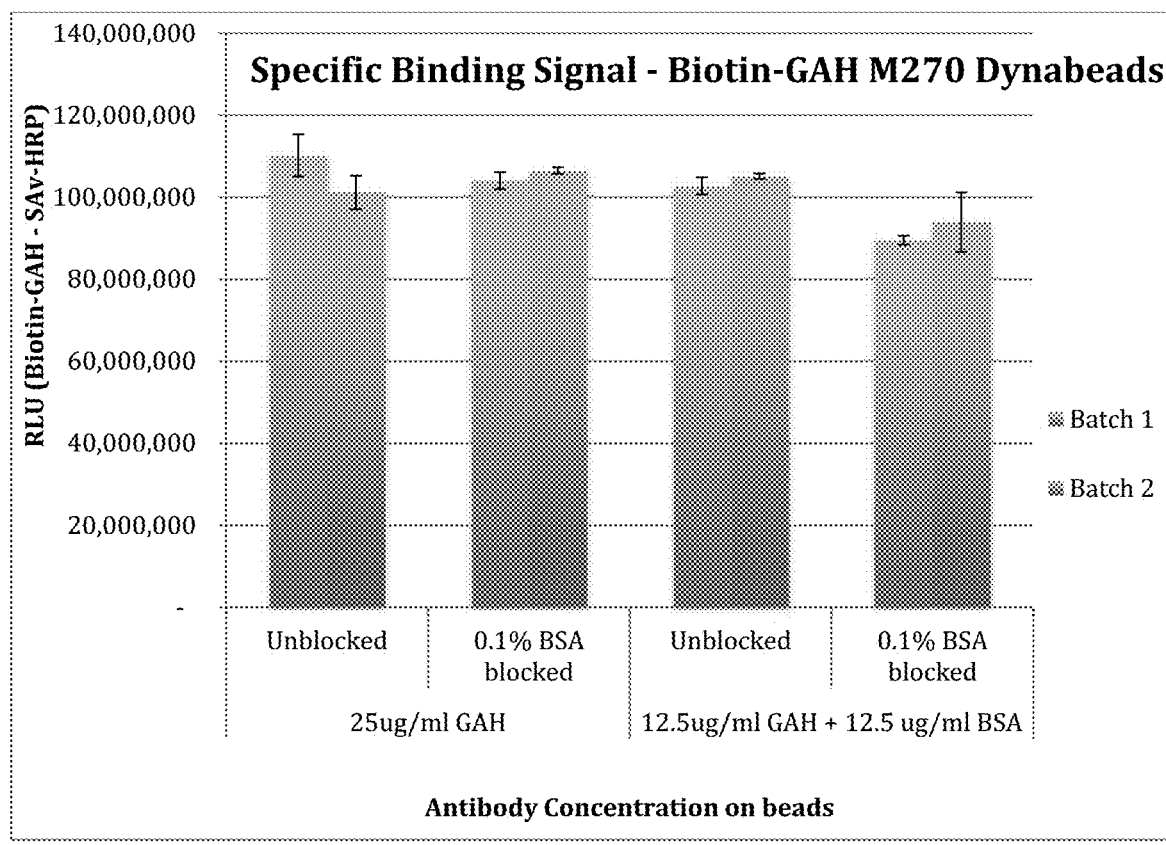
FIG. 6. Chemiluminescence assay data examining the signal output of certain concentrations of blocked and unblocked biotinylated-goat anti-human coupled to M270 Dynabeads.
Figure 7:
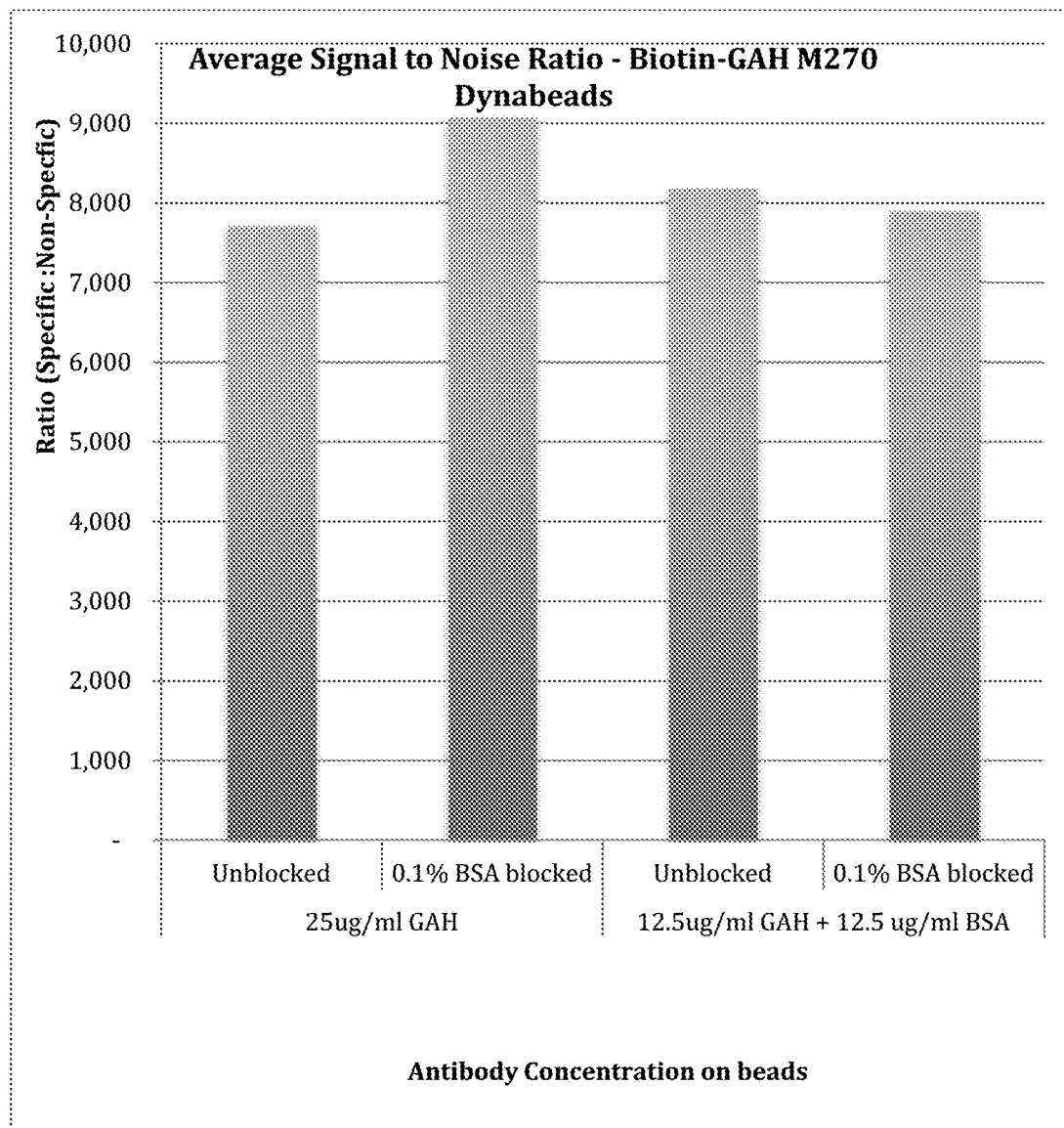
FIG. 7. Comparison of the specific signal to non-specific signal to noise ratio.

In the chemiluminescence assay results shown in FIGS. 6 and 7 (using HRP-conjugated streptavidin as the detection molecule and Lumigen PS-atto as the assay substrate) metal complex-activated particles displayed strong specific signal while also producing low background non-specific signal (an average signal to noise ratio of 9067×). The metal complex-activated M270 Dynabeads (coupled with 25 μg/mL biotinylated-goat anti-human and blocked with 0.1% BSA) were examined under a microscope at 40× magnification and at a concentration of 1 mg particles/mL and only minor insignificant aggregation was observed. Previous titrations and assays examining biotinylated-goat anti-human antibody loading on metal complex-activated M270 Dynabeads revealed that the particles were not showing an increase in signal when concentrations higher than 25 μg antibody/mL particle were coupled to the particles, indicating that the antibody loading was saturated at a concentration of 25 μg/mL. This loading concentration would be optimal for agglutination assays as there would be little or no metal complex binding sites available on these particles to interact with the other types of particles.

D-2. Preparation of Metal Complex-Activated MyOne Particles to Couple with Mouse IgG and BSA The co-coupling of goat anti-mouse antibody and BSA to metal complex-activated MyOne particles were prepared by activating MyOne carboxylated magnetic particles (Dynal) with 75 mM (final concentration) metal complex prepared according to section A, Example 2. MyOne particles (10 mg/mL) were activated at room temperature for 60 minutes. The particles were washed three times by 25 mM MES pH 6. The antibody was co-coupled at concentrations of 40 µg antibody, 20 µg antibody plus 20 µg BSA or 10 µg antibody and 30 µg per mg BSA per mg of metal complex-activated MyOne particles. The coated particles were incubated at room temperature for 60 minutes. The particles were then washed and stored in 10 mM TBS pH 8 at 4° C. Under the microscopy observation, the protein-coated particles were mono-dispersed (data not shown). The particles were assayed by binding to mouse anti-rabbit-HRP and read by multimode spectrophotometer (TECAN infinite M200PRO) with relative chemiluminescence unit as signal output in FIG. 8.

Figure 8:
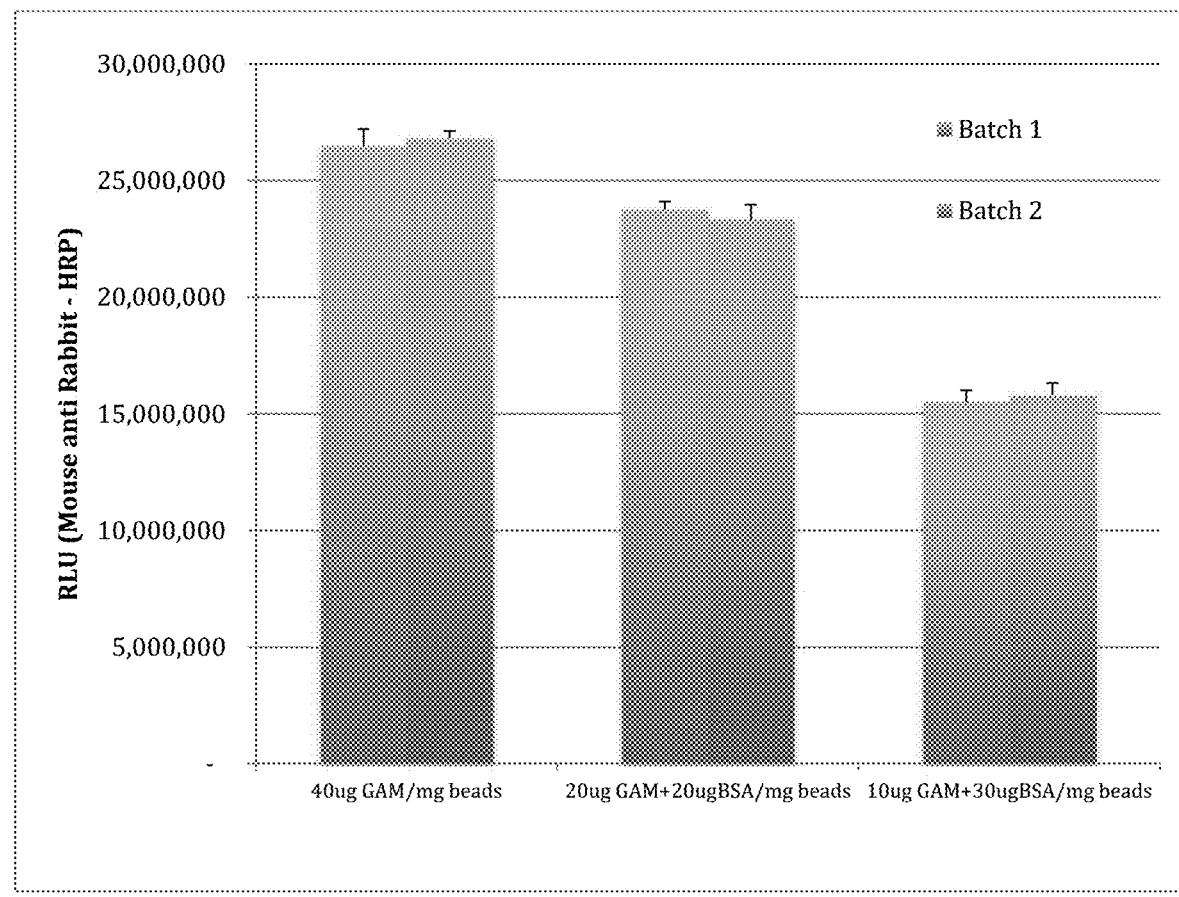
FIG. 8. Signal output of co-coupling of various concentrations of goat anti-mouse IgG and BSA to MyOne (Dynal, 1 μm) particles.

The result in FIG. 8 showed that the intensity of the signal output was related to the increase of goat anti-mouse IgG coupling concentrations. This result demonstrated that the loading amount of macromolecule, when coupling to metal complex-activated particles, can be controlled by a simple protein titration step in the coupling procedure without additional pH or time adjustments or chemical changes. The MyOne particles (20 µg antibody and 20 µg BSA) were selected to use in the agglutination assay (Section D-3, Example 2).

D-3. Agglutination Assay

Figure 9:
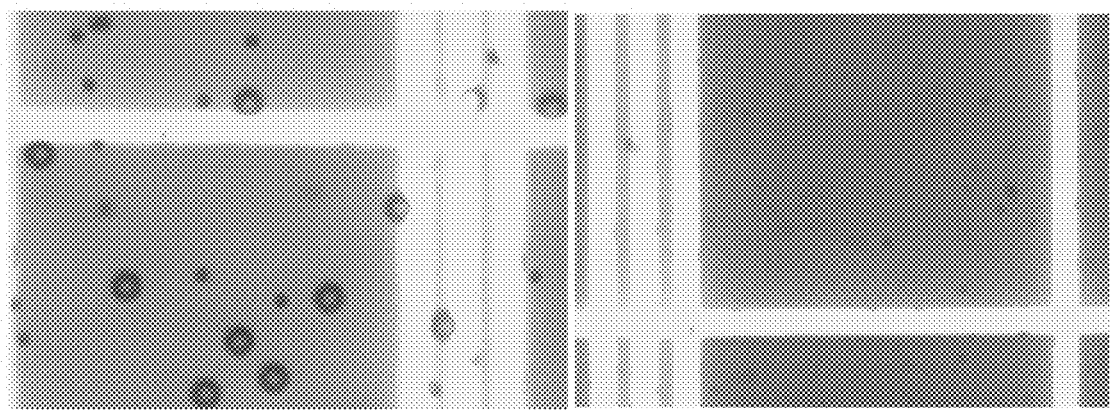
FIG. 9. M270 (3 μm), MyOne (1 μm) and Merck 200 nm particles before agglutination assay. Left: M270 (3 μm, larger particles) and MyOne (1 μm, smaller particles) after 1 hour incubation at room temperature; right: Merck 200 nm particles after 1 hour incubation at room temperature.
Figure 10:
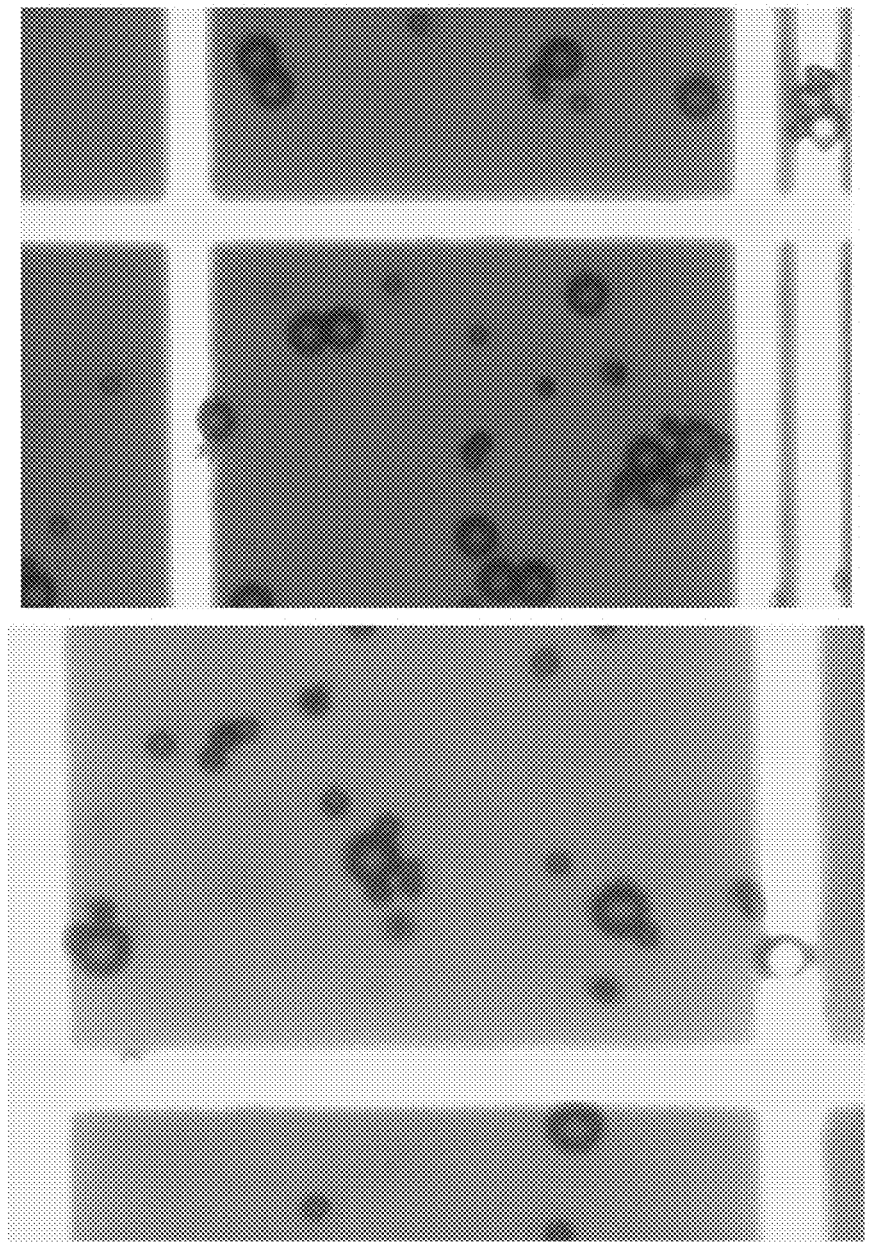
FIG. 10. Images of M270, MyOne, Merck bead mixture after 1 hour of incubation at room temperature. Aggregation of particles (large ones linked to small ones) can be observed clearly.

Three particles were used in the agglutination assays. They were M270 3 µm particles (25 µg/mL biotinylated-goat anti-human Dynabeads blocked with 0.1% BSA), MyOne 1 µm particles (Dynal 1 µm, 20 µg/mg goat anti-mouse co-coupled with 20 µg/mg BSA MyOne Dynabeads: from in-house preparation) and Merck 200 nm particles (Sample 2.11, 10 µg/mg streptavidin co-coupled with 10 µg/mg mouse IgG Merck M1-020/50 Estapor particles). The particles were assayed either in 10 mM PBS buffer pH 7.4 or 10 mM TBS pH 8, the final concentration for M270 particles was 6 mg/mL, MyOne particles was 2 mg/mL and Merck 200 nm particles was 2 mg/mL. The M270 particles were mixed with the MyOne particles at 1:1 particle ratio. The Merck particles were mixed with the mixture of M270 particles and MyOne particles at 1:1 particle ratio. Particle samples and mixtures were observed under a microscope (1000× magnification) at 4× dilution. The results are shown in FIGS. 9 and 10.

Agglutination is expected to occur between the particles due to reactivity between the molecules on the particles. If the Merck particles had indeed been co-coupled with streptavidin and mouse IgG via metal complex activation, and activity was retained, then the streptavidin on the Merck bead should link with the biotin on the M270 particles, and the mouse IgG of the Merck particles should link with the goat anti-mouse IgG of the MyOne particles. The expected result is that the three types of particles will aggregate causing significantly more clumps. However, if the streptavidin and mouse IgG were not successfully co-coupled onto the Merck particles and/or if the activity or conformation of the macromolecules was inhibited by the metal complex co-coupling interaction, then there should not be linking between particles.

The mixture of all three particles was compared to four control samples (biotinylated-goat anti-human antibody coupled to metal complex-activated M270 Dynabeads, goat anti-mouse antibody coupled to metal complex-activated MyOne Dynabeads, streptavidin co-coupled with mouse IgG to metal complex-activated Merck M1-020/50 200 nm particles, and a mixture of MyOne and Merck particles). Measurements were taken using a microscope at 400× magnification for the M270 particles and 1000× for the MyOne, Merck and the mixed bead samples, checking for aggregation after 10 minutes, 30 minutes and 1 hour of incubation with rotation and agitation.

All three control particles were mono-dispersed, showing almost no clumping. Similarly, the control particle mixture of M270 and MyOne particles also showed very little aggregation, indicating that any clumping in the mixture of three particles cannot be attributed to interaction between these two particles (one raw data video showed a MyOne bead "dancing" around some M270 particles but refusing to link with any of them; video not provided). On the other hand, the mixture of M270, MyOne and Merck particles showed lots of aggregates even after 10 minutes of incubation, suggesting that the activity of the two macromolecules on the Merck particles was not hindered and that they were able to bind successfully to those on the M270 and MyOne particles.

Two buffers were used for diluting the particles. Comparison of the particles and mixtures of particles diluted in PBS showed no difference to the same samples diluted in TBS. The aggregation of the three different particles in both buffers indicated that the co-coupled macromolecules were active in both environments and were viable for future chemiluminescence assays (requiring TBS buffer) and fluorescence assays (requiring PBS buffer). This agglutination result provided direct visual evidence to support the observation in section C, Example 2 that two marcomolecules (antibody and streptavidin) were co-coupled to metal complex-activated 200 nm magnetic particles successfully.

Example 3: Coupling Antibody and Streptavidin to Metal Complex-Activated 10-15 nm Superparamagnetic Iron Oxide Nanoparticles The aim of this example was to demonstrate that 10-15 nm iron oxide superparamagnetic nanoparticles can be activated by a metal complex, and then coupled with two different macromolecules, such as antibody and streptavidin.

A. Preparation of Metal Complex-Activated Iron Oxide Nanoparticles

Superparamagnetic iron oxide ($Fe_3O_4$) nanoparticles were purchased from SkySpring Nanomaterials, Inc in the US. Using a probe sonicator (3×10 seconds with 10 sec interval) an even suspension of iron oxide in water (440 mg/ml) was formed. To 390 µl of metal complex solution (as described in section A, Example 2) in an Eppendorf tube, 10 µl of stock iron oxide suspension was added slowly while constantly vortexing at low speed. The particles were vortexed for 30 seconds and sonicated for 5 minutes in a bath sonicator. The tube was incubated with rotation and after 1 hour, the probe sonicator was used for 3×10 seconds with a 10 seconds interval to form an even suspension. Using a magnet to pull down the particles, the particles were removed from the supernatant and 400 µl of 40 mM Universal Buffer pH 8 (coupling buffer) was added. The suspension was vortexed for 5 seconds and bath-sonicated for 1 minute. Supernatant was removed and 400 µl of 40 mM Universal Buffer pH 8 was added, and this process was repeated a total of three times. Particles were checked under a microscope.

B. Coupling of Streptavidin (with BSA) to Metal Complex-Activated a Nanoparticles The coupling protein was prepared in 40 mM coupling buffer prior to use. A mixture of streptavidin and BSA was coupled to the activated nanoparticle at different ratios and their final concentrations are listed in the table on the following page:

| | Streptavidin (μg per mg of particles) | BSA (μg per mg of particles) |
|---|---|---|
| Sample 3.1 | 400 | 0 |
| Sample 3.2 | 200 | 200 |
| Sample 3.3 | 100 | 300 |
| Sample 3.4 | 200 | 0 |
| Sample 3.5 | 100 | 100 |
| Sample 3.6 | 100 | 0 |

Figure 11:
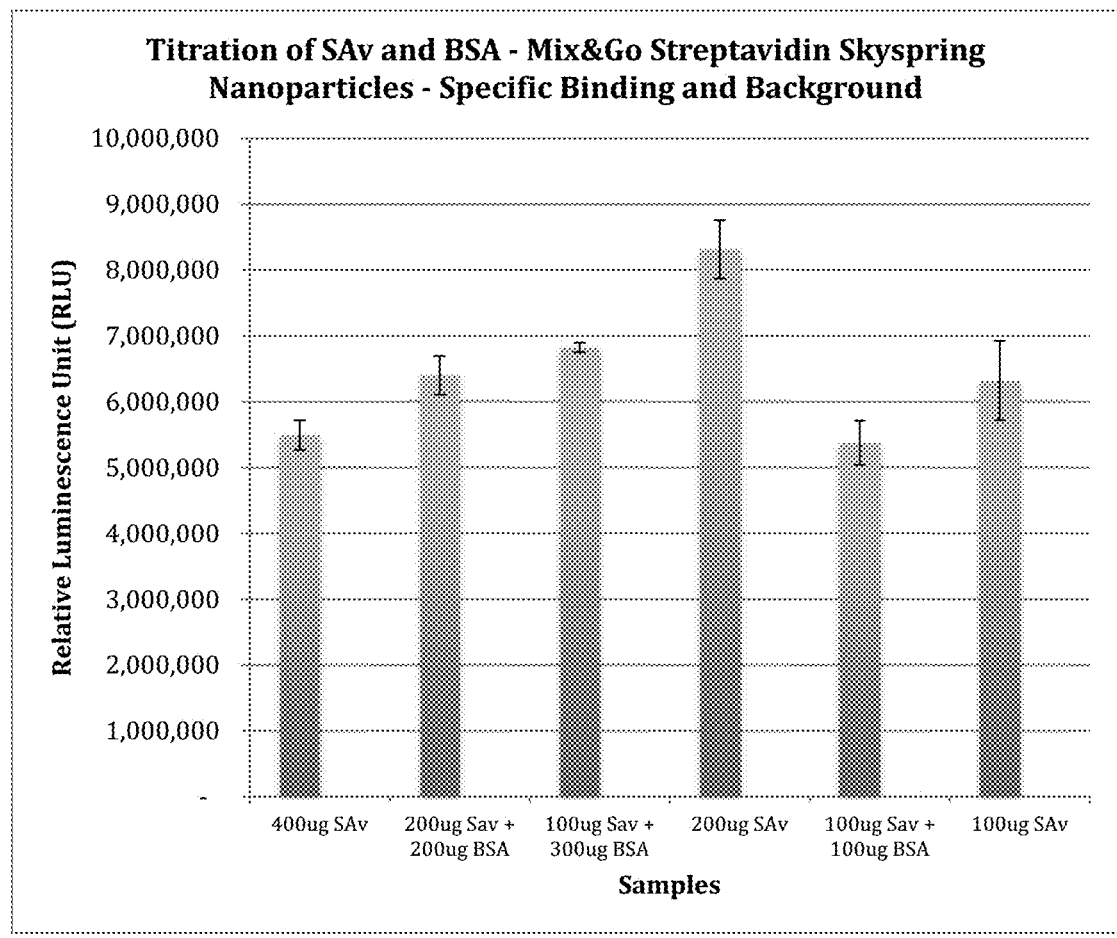
FIG. 11. Specific binding and background of co-coupling of streptavidin and BSA on metal complex-activated iron oxide nanoparticles.

The tube was vortexed with protein mixture on a low speed (No 3 setting on IKA Vortex GENIUS 3) while slowly adding 50 μL of washed particles to 50 μL of protein solutions listed in above table. The particle solution was vortexed for 30 seconds and bath-sonicated for 5 minutes. The particle solution was incubated with rotation (Rotator setting F5-90) for 1 hour at room temperature. The particles were washed with coupling buffer (pH 8) two times by magnetic separation. The particles were sonicated in a bath for 5 minutes. The particles were then checked under a microscope (5 μL of sample was diluted in 45 μL coupling buffer). Samples were assayed by binding to biotin-horseradish peroxidase, read by multimode spectrophotometer (TECAN infinite M200PRO) with relative chemiluminescence unit as signal output as shown in FIG. 11.

The results (FIG. 11) demonstrated that by varying concentrations of streptavidin loading to the metal complex-activated nanoparticles, the binding capacity was similar as streptavidin concentration increased while the BSA didn't have significant effect as a co-coupling blocker. The drop of signal in sample 3.1 was due to the aggregation and loss of particles during the process. Using BSA as co-coupling reagent seemed to interfere with the binding of streptavidin, which showed similar effect in section B, Example 2. All six samples all showed very low background which indicated that the nanoparticles are fully loaded or blocked with proteins. The result from sample 3.4 and 3.6 demonstrated that the amount of streptavidin in direct coupling to metal complex-activated surface can be controlled without additional pH adjustment or chemical composition changes.

C. Coupling of Mouse IgG (with BSA Blocker) to Metal Complex-Activated Nanoparticles The coupling protein solution was prepared prior to use. A mixture of mouse IgG and BSA were coupled to the metal complex-activated nanoparticle at different ratios listed in the table below:

| | Antibody - mouse IgG (μg per mg of particles) | BSA (μg per mg of particles) |
|---|---|---|
| Sample 3.7 | 200 | 200 |
| Sample 3.8 | 100 | 300 |
| Sample 3.9 | 200 | 0 |
| Sample 3.10 | 100 | 100 |
| Sample 3.11 | 100 | 0 |
| Sample 3.12 | 50 | 50 |

Figure 12:
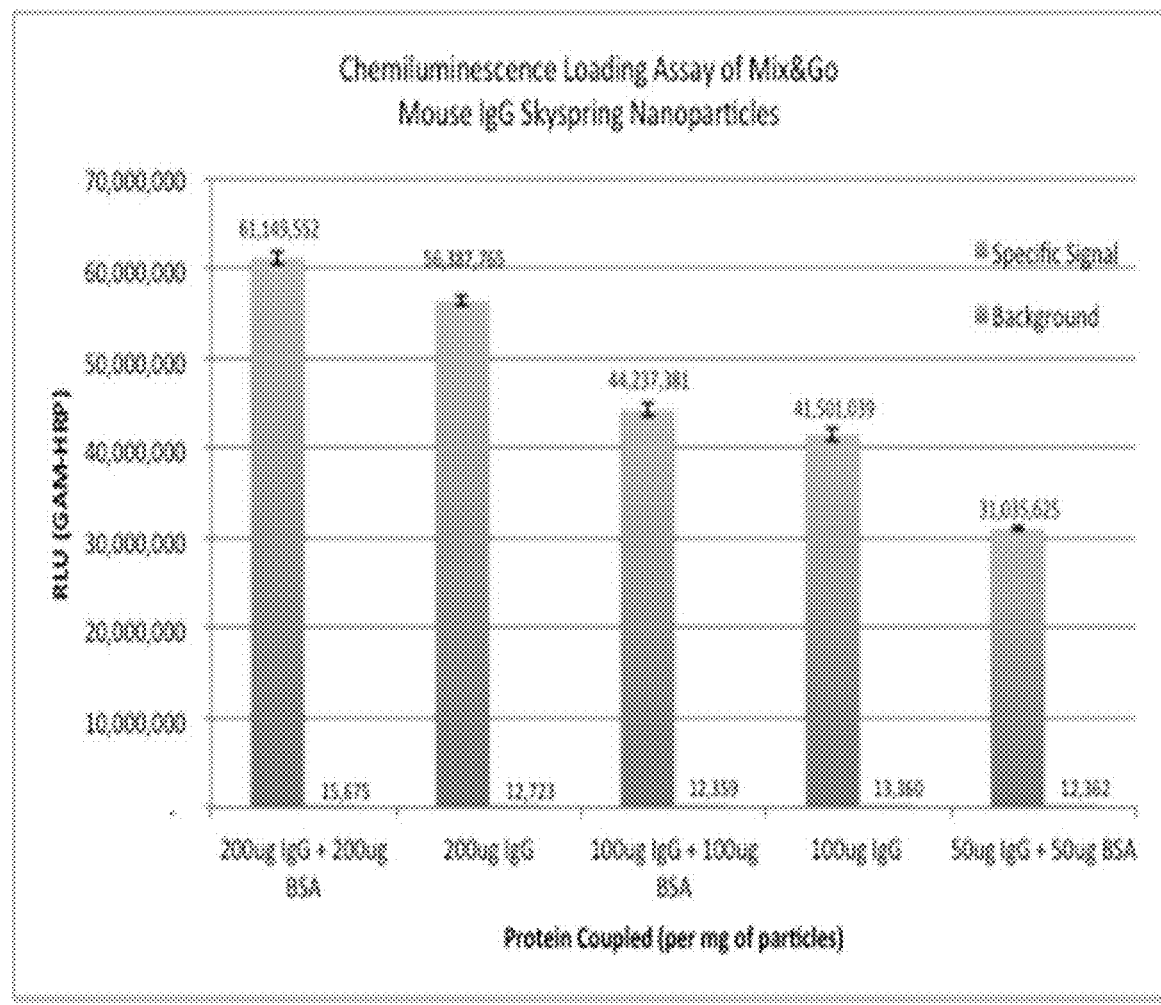
FIG. 12. Signal and background noise of coupling various concentrations of mouse IgG on metal complex-activated iron oxide nanoparticles FIG. 13. Co-coupling of streptavidin and mouse IgG on iron oxide nanoparticles using goat anti-mouse-conjugated RPE for fluorescence signal output.

The coupling steps in section B, Example 3 were repeated. Samples were assayed by binding to goat anti-mouse conjugated horseradish peroxidase; read by a multimode spectrophotometer (TECAN infinite M200PRO) with relative chemiluminescence unit as signal output, the results were shown in FIG. 12.

The results (FIG. 12) demonstrated that by varying concentrations of antibody loading to the metal complex-activated nanoparticles, the binding capacity increased as mouse IgG coupling concentration increased while the BSA didn't have significant effect as a co-coupling blocker. All five conditions all showed very low background which indicated that the nanoparticles are fully loaded or blocked with proteins. It also showed that mouse IgG had stronger binding affinity in comparison to BSA. So, the results demonstrated that the mouse IgG binding capacity onto iron oxide nanoparticles could be controlled and co-coupling of a blocker was also achieved by a simple protein concentration titration step in the coupling procedure without additional pH adjustment or chemical composition changes.

D. Coupling of Antibody and Streptavidin to Metal Complex-Activated Nanoparticles The coupling protein was prepared prior to use in 40 mM coupling buffer. A mixture of streptavidin and mouse IgG were coupled to the metal complex-activated nanoparticle at different ratios as per the table below:

| | Streptavidin (μg/per mg of particles) | Antibody - mouse IgG (μg/per mg of particles) |
|---|---|---|
| Sample 3.14 | 300 | 100 |
| Sample 3.14 | 200 | 200 |
| Sample 3.15 | 100 | 300 |

In addition, BSA or PEG was coupled to the activated nanoparticle at different concentrations as listed in the table below:

| | BSA (μg/per mg of particles) | PEG (μg/per mg of particles) |
|---|---|---|
| Sample 3.16 | 200 | 0 |
| Sample 3.17 | 0 | 1000 |

The coupling steps in section B, Example 3 were repeated. Protein coupled samples were assayed by binding to biotin-REP or goat anti-mouse-RPE, read by multimode spectrophotometer (TECAN infinite M200PRO) with relative fluorescence unit as signal output. The results are shown in FIG. 13 and FIG. 14.

Figure 13:
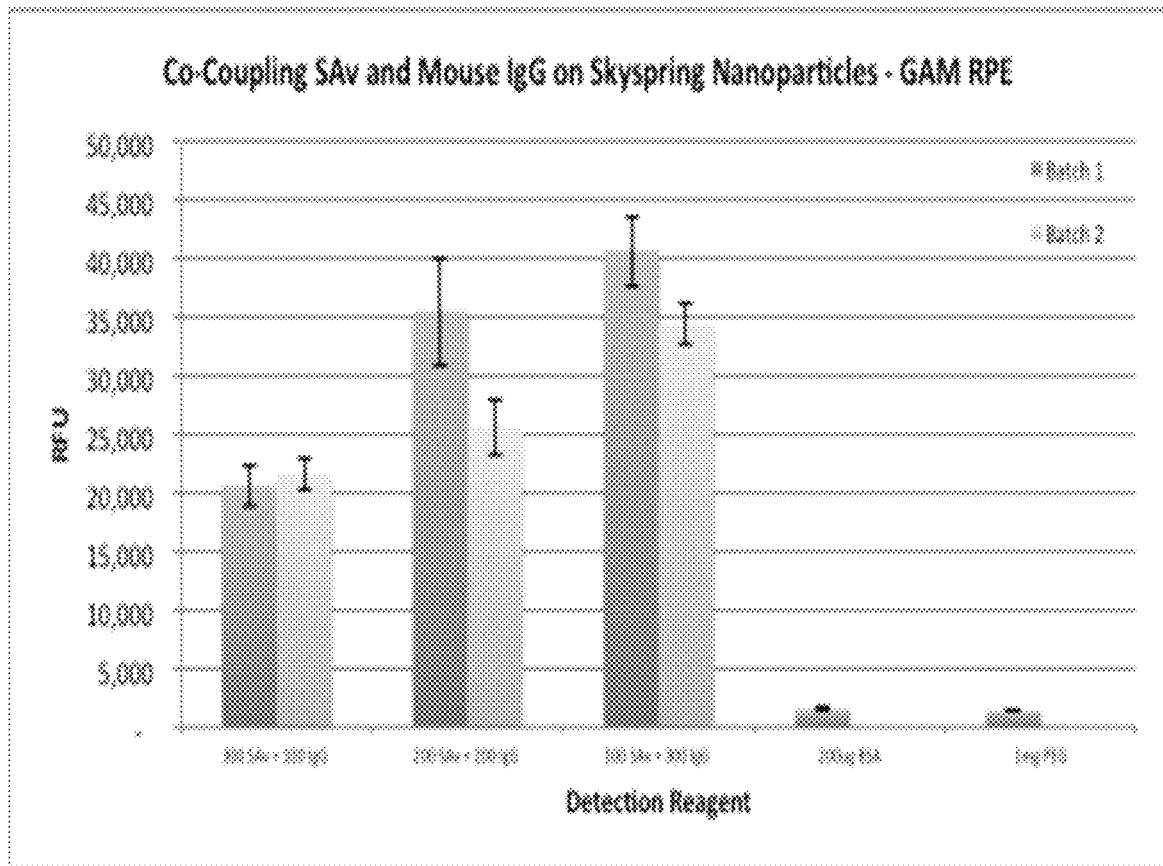
Figure 14:
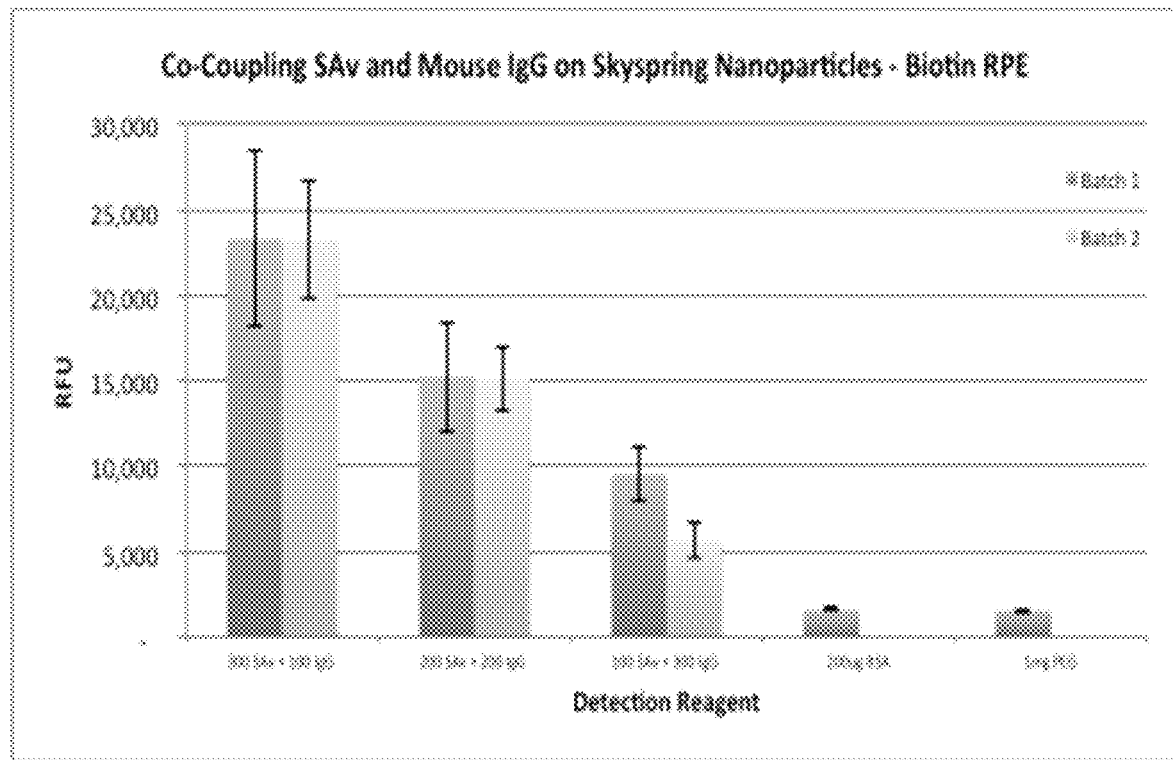
FIG. 14. Co-coupling of streptavidin and mouse IgG on iron oxide nanoparticles using biotin-conjugated RPE for fluorescence signal output.

The result from FIGS. 13 and 14 both showed that the specific signal output was strongly related to the increase of mouse IgG or streptavidin coupling concentrations. In FIGS. 13 and 14, both the negative controls (200 μg BSA/mg of particles and 1 mg PEG/mg of particles) were working as expected and showed the relatively low background. This result also demonstrated that the amount of macromolecule such as streptavidin and mouse IgG co-coupling to metal complex-activated particles could be controlled by a simple protein titration step in the coupling procedure without additional pH or time adjustments or chemical composition changes.

Example 4: Metal Complex on Gold Nanoparticles and Subsequent Binding to Antibodies The aim of this example is to demonstrate that metal complex-activated gold nanoparticles can bind to one or two macromolecules such as antibodies.

Two gold nanoparticles samples were sourced from Sigma Aldrich. One, surfactant stabilised gold nanoparticles stored in citrate buffer; the second, bare gold nanoparticles stored in PBS buffer. Both samples were concentrated and excess supernatant removed. The nanoparticles were then re-suspended in water. The gold nanoparticles were activated in metal complex at OD1 for one hour at room temperature. Excess metal complex was washed away by centrifugation. The following conditions were setup in the coupling procedure per 1 mL of OD1 gold nanoparticles:

Sample 4.1: 3.2 µg of human IgG antibody;
Sample 4.2: 3.2 µg of mouse IgG antibody;
Sample 4.3: 1.6 µg of human IgG plus 1.6 µg of mouse IgG.

Each antibody condition was prepared in 10 mM MES buffer pH 6.0 and was coupled and incubated at room temperature for thirty minutes. The coupled samples were concentrated and resuspended in 2 mM borax buffer pH 9.0. Dipsticks (nitrocellulose based) striped with goat anti-mouse antibody, anti-human IgM and anti-human IgG were used to detect antibody loading on metal complex-activated gold nanoparticles. The antibody coupled gold samples were diluted out to OD1 in PBS buffer with 1% Tween-20. 50 µL of each sample was loaded into a 96 well plate, after which the dipsticks were placed into each well and were allowed to run for ten minutes.

Figure 15:
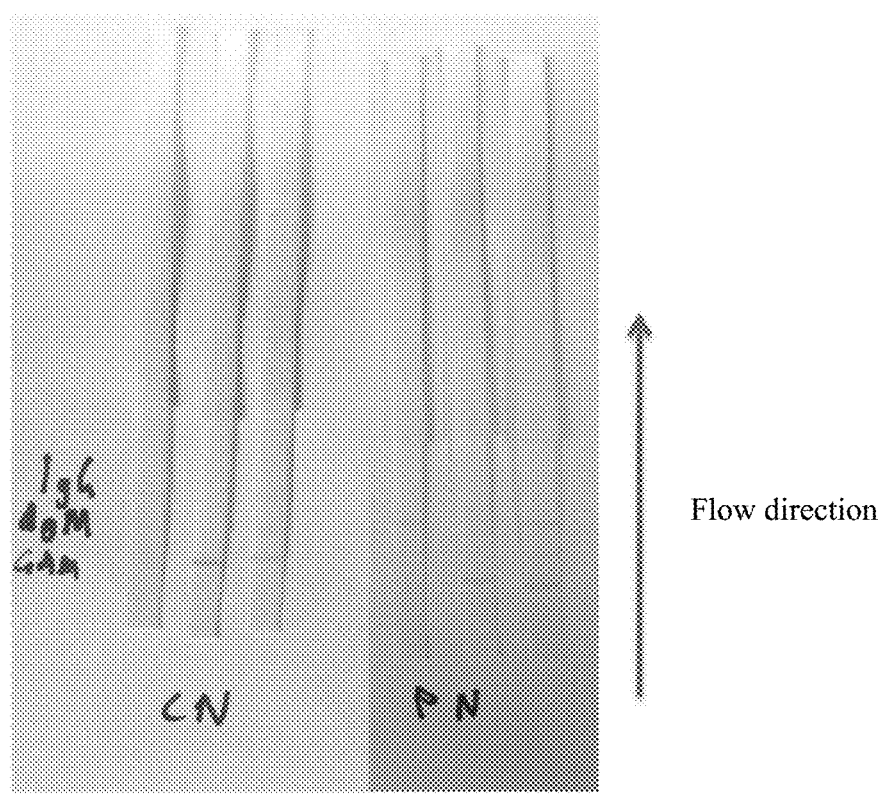
FIG. 15. Dipstick assays of coupling antibodies on metal complex-activated gold nanoparticles.

The result is shown in FIG. 15. From the result, samples order from left to right in each setting is (1), (2) and (3). The citrate buffered gold nanoparticles (CN) look similar to the PBS buffered samples (PN). In each activation condition the bands corresponding to the anti-human IgG mark were much lighter than the goat anti-human band in both the single and combined antibody couplings. The dipstick bands intensities of samples coupled with a single antibody were comparable to that of the co-coupled samples, while no non-specific was observed. As expected, the sample 4.1 and sample 4.2 both showed a single band with not observable non-specific binding. The sample 4.3 showed two bands and the intensity was similar to sample 4.1 and 4.2, this indicated that mouse IgG and human IgG both coupled to gold nanoparticles and the particles were not captured by first anti-mouse IgG line was flowing through to be captured by anti-human IgG line. The result demonstrates that using the metal complex activation process, one or two different antibodies were coupled to the gold nanoparticle and observed by a lateral flow antibody immunoassay.

Example 5: Metal Complex on 200 nm Magnetic Nanoparticles and Subsequent Binding to Antibodies and Enzymes The aim of this example is to demonstrate that metal complex-activated 200 nm magnetic nanoparticles such as Merck (200 nm) nanoparticles can bind to one kind of antibodies and one kind of enzymes simultaneously (for example, anti-TNF alpha antibody and horseradish peroxidase).

Figure 16:
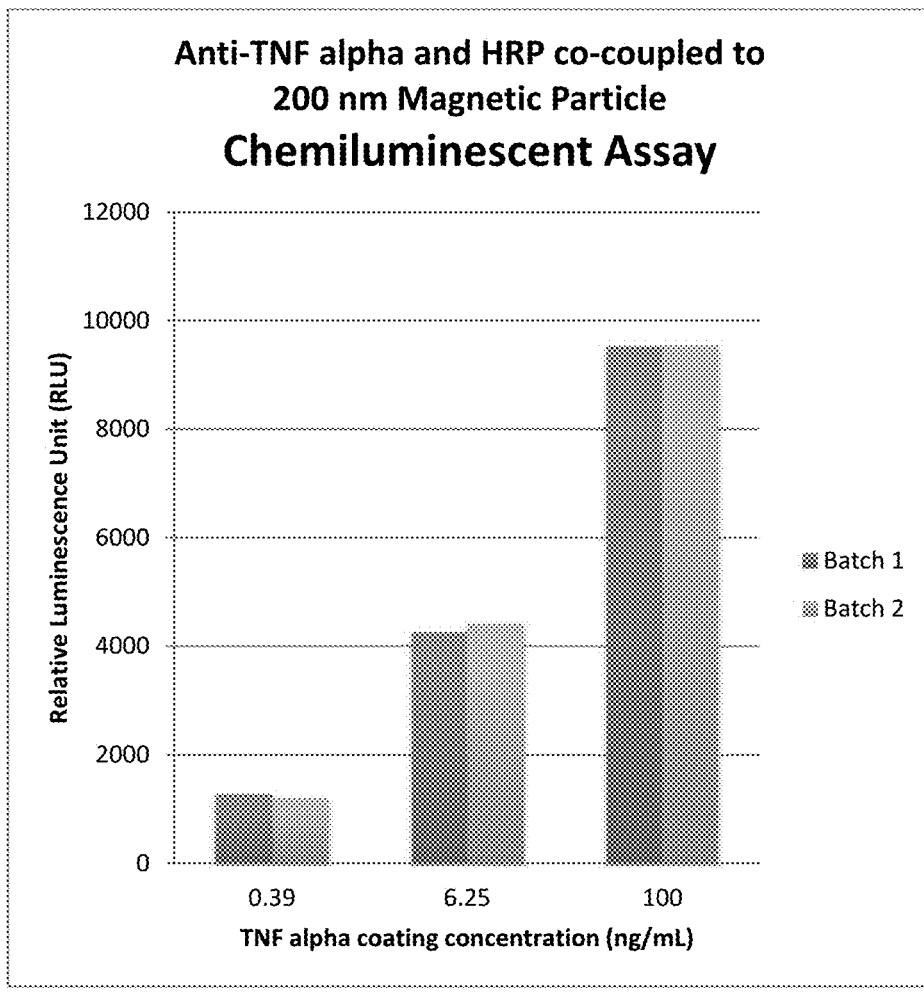
FIG. 16. TNF-alpha sandwich immunoassays using detection of anti-TNF-alpha antibodies and horseradish peroxidase on metal complex-activated magnetic particles.

The preparation of metal complex-activated 200 nm magnetic particles is described in Example 2A. Anti-TNF alpha antibodies (20 µg/mg of particles) were co-coupled with horseradish peroxidase (20 µg/mg of particles) to metal complex-activated 200 nm magnetic particles and blocked by 0.1% BSA. The Maxisorp plate (from NUNC) was coated with TNF-alpha antigens at 0.39, 6.25 and 100 ng/mL in carbonate buffer pH 9.5 for one hour. Then the plate was blocked by 1% BSA in PBS 7.2 for one hour. The Antibody-HRP conjugated particles (25 µg/mL) were diluted in the assay buffer 1% BSA PBS pH 7.2 and added to the ELISA wells coated with TNF-alpha and incubated at room temperature for one hour. The plate was washed by PBS pH 7.2 with 0.05% Tween-20 three times before adding 100 µl PS-Atto (Pierce) chemiluminescent substrate each well, shaking for one minutes before read by multimode spectrophotometer (TECAN infinite M200PRO) with relative luminescence unit as signal output. The background corrected results are shown in FIG. 16. The result from FIG. 16 showed that the specific signal output was strongly related to the increase of TNF-alpha amount coated on the plate. This result also demonstrated that the both anti TNF-alpha antibodies and HRP were coupled to the same particles in order to perform antibody antigen binding and the HRP acts as detection enzyme to generate signal. This also demonstrates that metal complex-activated magnetic nanoparticles can couple two different macromolecules (antibodies and enzyme) onto one particle simultaneously and both show functionality after coupling.

Example 6: Metal Complex on Magnetic Nanoparticles and Subsequent Binding to QDot Nanoparticles The aim of this example is to demonstrate that metal complex-activated 200 nm magnetic nanoparticles such as Merck (200 nm) nanoparticles can bind to other nanoparticles (for example, Quantum dots).

Figure 17:
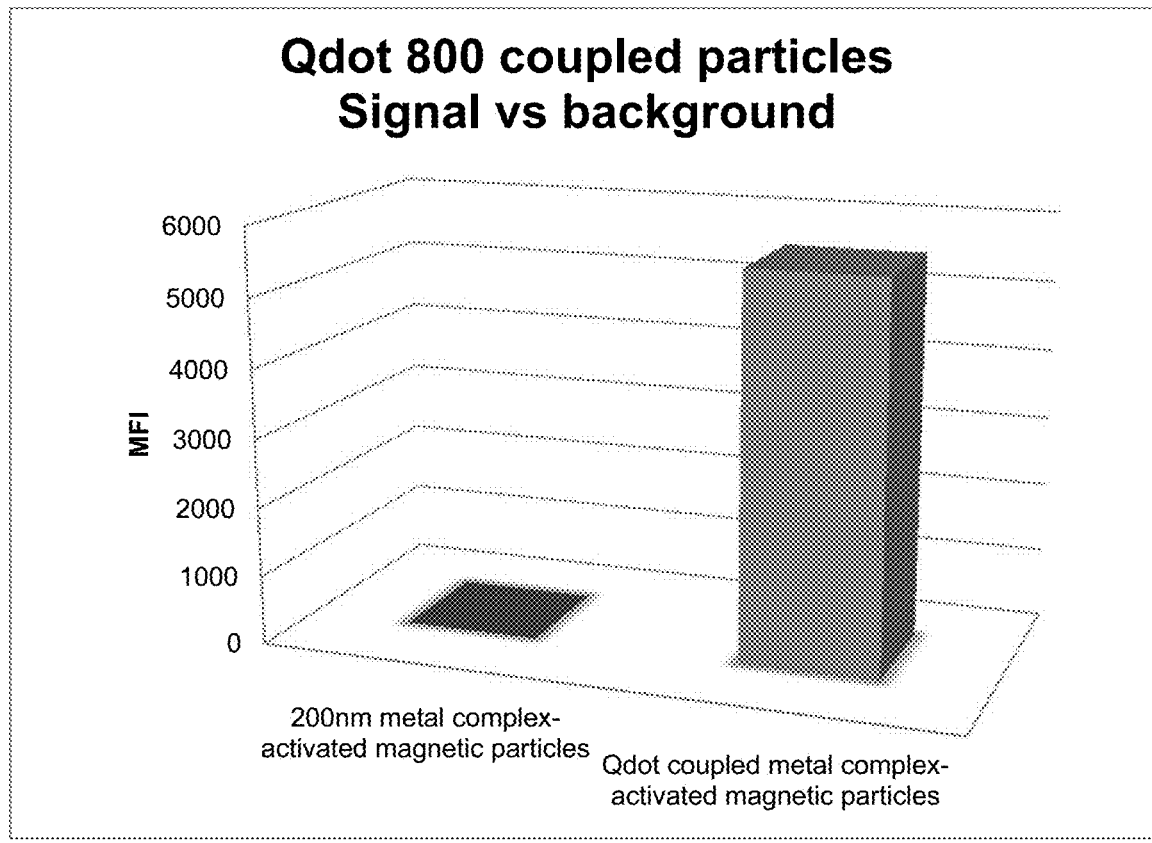
FIG. 17. Coupling of Quantum dots (QDots) on metal complex-activated magnetic particles for fluorescence signal output.

The preparation of metal complex-activated 200 nm magnetic particles is described in Example 2A. The Quantum dots 800 (carboxylic acid modified, Life Technologies) 1000 pmoles/mg magnetic particles were mixed and incubated at room temperature for one hour. Excess QDots were washed away by water and the QDot coupled metal complex-activated magnetic particles were read by TECAN infinite M200PRO at excitation 415 nm and emission 800 nm. FIG. 17 shows the result of QDot intensity signal to noise ratio when compared to metal complex-activated magnetic particles. The signal to noise ratio is 5570:1 after normalisation, which indicates that the QDots have been coupled to metal complex-activated magnetic particles successfully and demonstrates that metal complex-activated surface can bind to another nanoparticles such as QDots.

Figure 18:
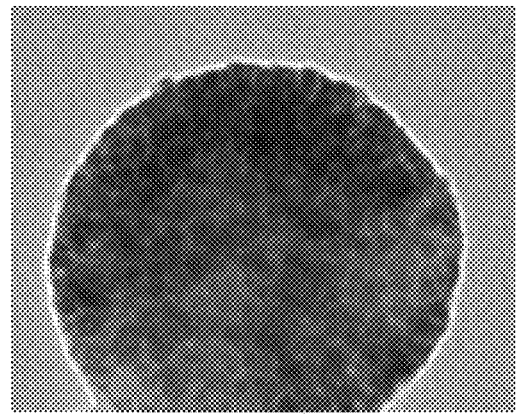
FIG. 18. TEM images of metal complex-activated magnetic particles with or without coupling to QDots.
Figure 18:
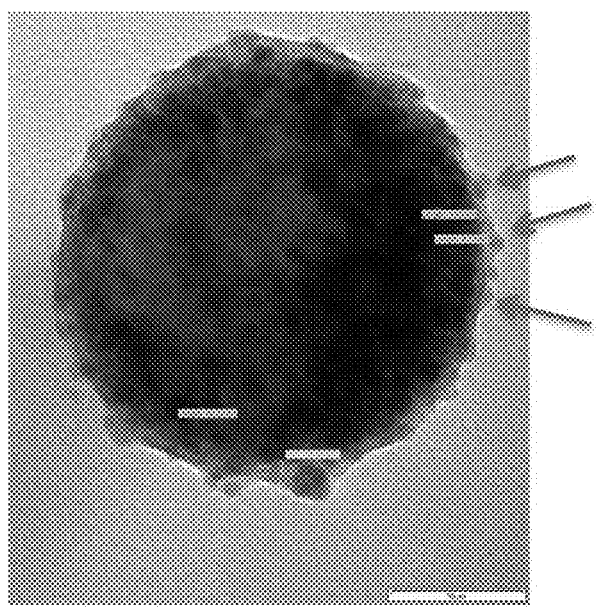

The transmission electronic microscopy (TEM) images were performed on these samples. A drop of the sample was applied to the carbon coated copper TEM grid for 1-2 min and the excess removed. A drop of stain was then applied, either uranyl acetate or ammonium molybdate, for 5-60 sec and the excess removed. Best results were achieved with uranyl acetate. Accelerating voltage 80 kV and magnification to ×600,000 on all samples to allow resolution of <2 nm. FIG. 18 shows the results of TEM. From the TEM result, it shows that the metal complex-activated surface is smooth and QDot coupled magnetic particles have QDot size on the surface as indicated by arrows. This demonstrates that carboxylic acid surface modified QDots have been coupled to metal complex-activated magnetic particles successfully and the QDot signal intensity characteristics can be observed.

The invention claimed is:
1. A nanoparticle including:
a surface including ligands, wherein said ligands include an electron-donating group;
transition metal ions at least partially coating the surface; and
a first target molecule and a second target molecule, wherein the first and second target molecules are different to each other and are present on the nanoparticle in a predetermined ratio,
wherein the nanoparticle includes a substrate formed from one or more substrate molecules or atoms; and
wherein, through the transition metal ions, co-ordination bonds are formed between; (i) the ligands including the electron-donating group at the nanoparticle surface and the first target molecule; and (ii) the ligands including the electron-donating group at the nanoparticle surface and the second target molecule; thereby separately linking the first and second target molecules to the nanoparticle surface; and the nanoparticle further including a ligand, wherein the ligand for the transition metal ions is selected from the group consisting of: ethylenediamine, tetramethylethylenediamine, iminodiacetic acid, nitrilotriacetic acid, triphenylphosphine, oxalic acid, 1,10-phenanthroline, 8-hydroxyquinoline, salicylic acid, chloride, acetate, bromide, nitrate, perchlorate, alum, sulphate and pyridine.

2. The nanoparticle of claim 1, wherein the nanoparticle has a diameter of about 5 to about 200 nm.

3. The nanoparticle of claim 1, wherein the transition metal ion is selected from aluminum, rhodium, platinum, scandium, titanium, vanadium, chromium, ruthenium, manganese, iron, cobalt, nickel, copper, molybdenum, zirconium and zinc.

4. The nanoparticle of claim 3, wherein the transition metal ion is chromium.

5. The nanoparticle of claim 1, wherein each of the first and second target molecules is selected independently from a protein, a polynucleotide, a carbohydrate, a lipid, a drug, a labelling agent, a synthetic polymer and a nanoparticle.

6. A composition including:
a nanoparticle including a substrate formed from one or more substrate molecules or atoms, wherein the surface of the nanoparticle includes ligands which include an electron-donating group;
a ligand having a group for forming a co-ordination bond with a transition metal ion; and
a transition metal ion for forming a co-ordination bond with the one or more substrate molecules or atoms; a first target molecule and a second target molecule, wherein the first and second target molecules are different to each other;

wherein, through the transition metal ions, co-ordination bonds are formed between: (i) the ligands including the electron-donating group at the nanoparticle surface and the first target molecule; and (ii) the ligands including the electron-donating group at the nanoparticle surface and the second target molecule; thereby separately linking the first and second target molecules to the nanoparticle surface; wherein the first and second target molecules are present on the nanoparticle in a predetermined ratio; and wherein the ligand for the transition metal ions is selected from the group consisting of: ethylenediamine, tetramethylethylenediamine, iminodiacetic acid, nitrilotriacetic acid, triphenylphosphine, oxalic acid, 1,10-phenanthroline, 8-hydroxyquinoline, salicylic acid, chloride, acetate, bromide, nitrate, perchlorate, alum, sulphate and pyridine.

7. The composition of claim 6, wherein the particle has a diameter of about 5 to about 200 nm.

8. The composition of claim 6, wherein the ligand is ethylenediamine.

9. The composition of claim 6, wherein the transition metal ion is selected from aluminum, rhodium, platinum, scandium, titanium, vanadium, chromium, ruthenium, manganese, iron, cobalt, nickel, copper, molybdenum, zirconium and zinc.

10. The composition of claim 9, wherein the metal ion is chromium.

11. The composition of claim 6, wherein the first and second target molecules are independently selected from a protein, a polynucleotide, a carbohydrate, a lipid, a drug, a labelling agent, a synthetic polymer and a nanoparticle.

12. The nanoparticle of claim 1, wherein the substrate molecule is selected from a synthetic polymer, a metal or metalloid composite, a biological material, ceramic, glass and metal oxide.

13. The nanoparticle of claim 1, wherein the substrate atom is selected from gold, silicon and carbon.

* * * * *